United States Patent
Colley

(10) Patent No.: US 11,780,079 B2
(45) Date of Patent: Oct. 10, 2023

(54) FLEXIBLE STRUCTURE, PARTICULARLY FOR APPLICATIONS IN ROBOTICS AND ORTHOPEDICS

(71) Applicant: John Christian Colley, Trafford, PA (US)

(72) Inventor: John Christian Colley, Trafford, PA (US)

( * ) Notice: Subject to any disclaimer, the term of this patent is extended or adjusted under 35 U.S.C. 154(b) by 0 days.

(21) Appl. No.: 17/692,164

(22) Filed: Mar. 10, 2022

(65) Prior Publication Data
US 2023/0286134 A1 Sep. 14, 2023

(51) Int. Cl.
*B25J 9/00* (2006.01)
*A61F 5/01* (2006.01)

(52) U.S. Cl.
CPC ..... *B25J 9/0015* (2013.01); *A61F 2005/0132* (2013.01)

(58) Field of Classification Search
CPC ... B25J 9/0015; A61F 2005/0132; F16F 3/00; F16F 3/08; F16F 3/087; F16F 3/0873; F16F 3/0876; F16F 3/093; F16F 3/0935; F16F 1/3615; F16F 1/3713; F16F 1/3716; F16F 1/14; F16F 1/145; F16F 1/16; F16F 1/18; F16F 1/182; F16F 1/187; F16F 1/26; F16F 1/28; F16F 1/30; F16F 1/36; F16F 1/3605; F16F 1/368; F16F 1/3683; F16F 1/3686; F16F 1/371; F16F 1/373; F16F 1/376; F16F 1/3821; F16F 1/3814; F16F 1/387; F16F 1/393; F16F 1/3935; F16F 1/406; F16F 1/428; F16F 7/082; F16F 7/087
USPC ............................................... 74/490.05, 470
See application file for complete search history.

(56) References Cited

U.S. PATENT DOCUMENTS

| | | | |
|---|---|---|---|
| 3,060,972 A | 10/1962 | Sheldon | |
| 3,118,659 A * | 1/1964 | Paulsen | B60G 7/04 267/35 |
| 3,266,059 A | 8/1966 | Stelle | |
| 3,272,492 A * | 9/1966 | Jones | F16F 3/02 464/84 |
| 3,751,066 A * | 8/1973 | Narahari | B60G 11/465 267/243 |

(Continued)

FOREIGN PATENT DOCUMENTS

| | | | |
|---|---|---|---|
| DE | 4035780 A1 * | 10/1990 | |
| DE | 20000403 U1 * | 5/2001 | A47C 23/002 |

(Continued)

*Primary Examiner* — T. Scott Fix

(57) ABSTRACT

A flexible structure that exhibits axial, bending, and twisting compliance, allowing for limited freedom of deformation and impact load dampening characteristics tailored accordingly for the applications of the flexible structure. The flexible structure comprises two or more formers, a plurality of resilient members supporting and affixed to the perimeters of the formers, and either an elastomeric central member located between each former and in the center of the resilient members, or an elastomeric surrounding member located between each former and around the resilient members, or both. The presence of the central member or surrounding member acts to inhibit excessive deformations of the resilient members through contact forces. This construction provides a strong and flexible structure that can be incorporated with robots, orthopedic braces, and other devices.

3 Claims, 21 Drawing Sheets

(56) References Cited

U.S. PATENT DOCUMENTS

| | | | |
|---|---|---|---|
| 3,879,025 A | 4/1975 | Dillard | |
| 4,717,288 A | 1/1988 | Finn | |
| 4,815,911 A * | 3/1989 | Bengtsson | B25J 18/06 |
| | | | 446/368 |
| 5,149,066 A | 9/1992 | Snaith | |
| 5,280,890 A | 1/1994 | Wydra | |
| 5,445,471 A | 8/1995 | Wexler | |
| 5,728,023 A * | 3/1998 | Green | F16G 13/02 |
| | | | 474/206 |
| 6,578,835 B2 | 6/2003 | Monson | |
| 8,708,593 B2 | 4/2014 | Stratton | |
| 10,624,530 B2 * | 4/2020 | Graham | A01K 85/005 |
| 10,677,307 B2 | 6/2020 | Aagaard | |
| 2010/0301531 A1 * | 12/2010 | Delahousse | F16F 1/027 |
| | | | 267/165 |
| 2016/0368342 A1 * | 12/2016 | Nolte | F16F 1/44 |
| 2019/0195304 A1 * | 6/2019 | Dubost | B64C 1/18 |

FOREIGN PATENT DOCUMENTS

| | | | | |
|---|---|---|---|---|
| DE | 19962026 A1 * | 6/2001 | | B60G 15/06 |
| DE | 102013017708 A1 * | 4/2015 | | F16F 1/14 |
| EP | 2072851 A2 * | 6/2009 | | F16F 1/3737 |
| EP | 2082903 A2 * | 7/2009 | | B60G 11/00 |
| GB | 2537501 A * | 10/2016 | | B60P 1/64 |
| JP | H-03234937 A * | 10/1991 | | |
| JP | 2726710 B2 * | 9/1997 | | |
| KR | 200372165 Y1 * | 1/2005 | | |
| WO | WO-8500207 A1 * | 1/1985 | | |
| WO | WO-9315332 A1 * | 8/1993 | | F16F 1/373 |

* cited by examiner

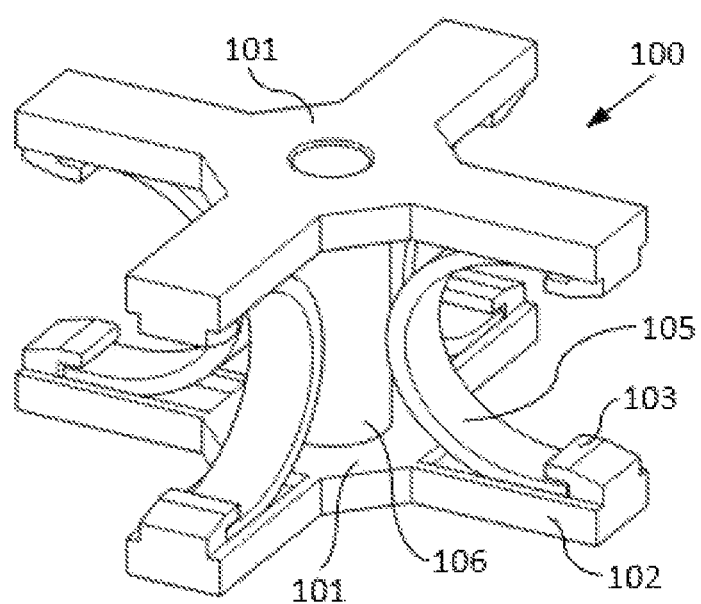
FIG. 1-A

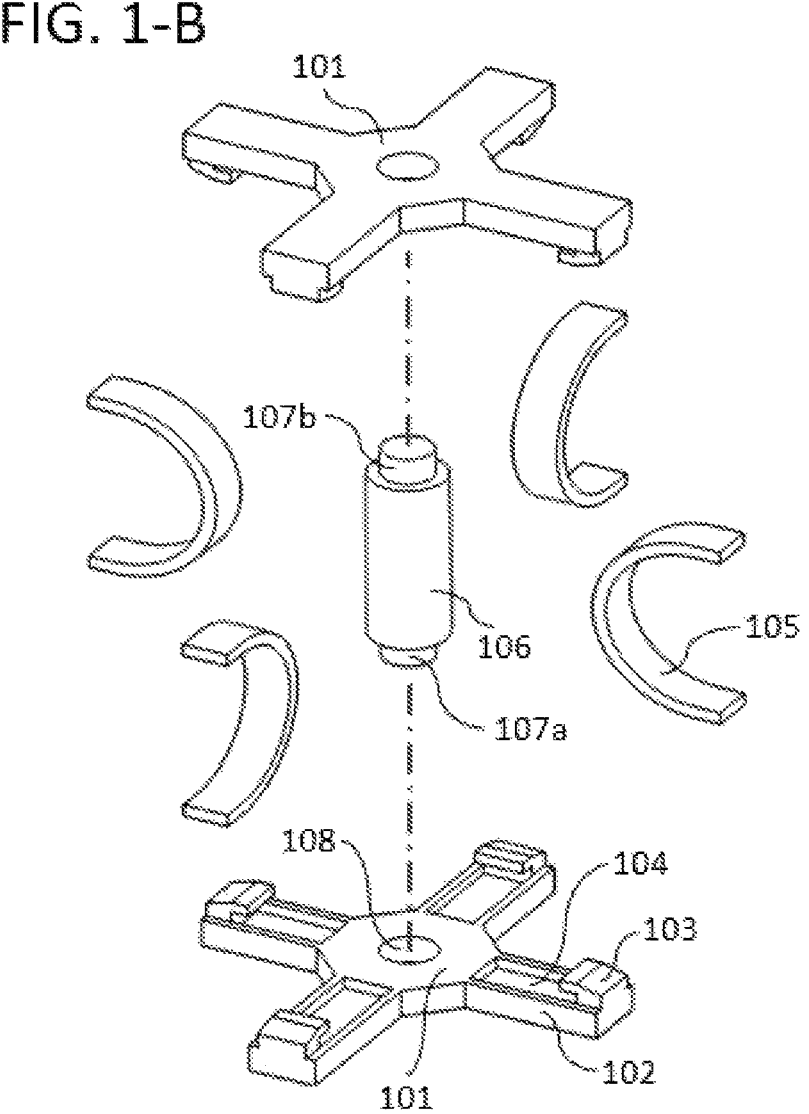

FIG. 2-A
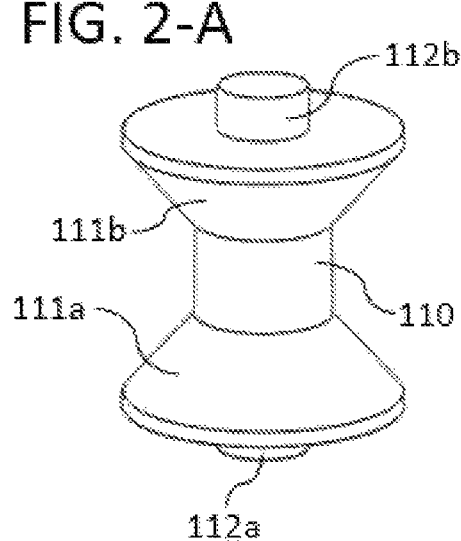
FIG. 2-B
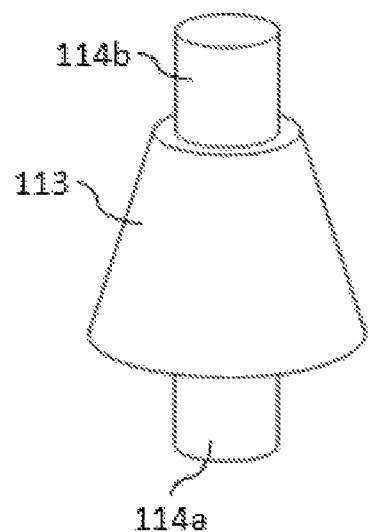
FIG. 2-C
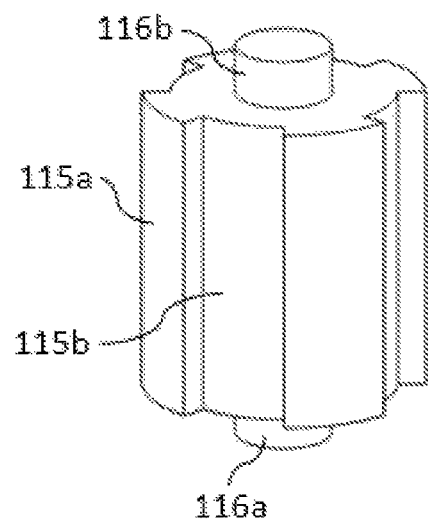
FIG. 2-D
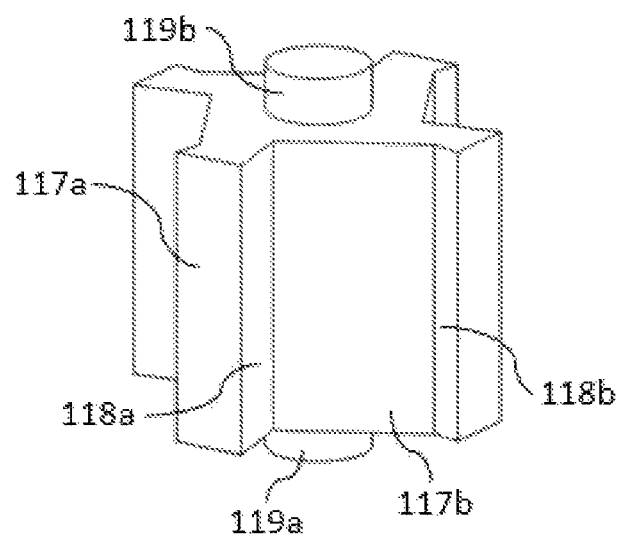

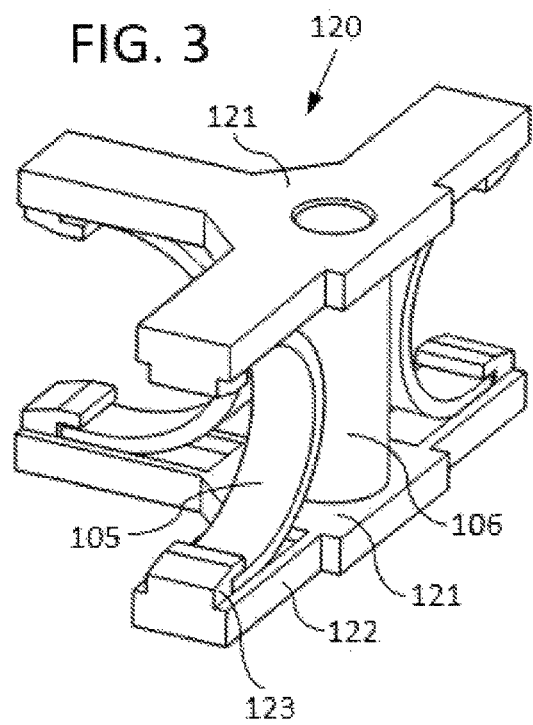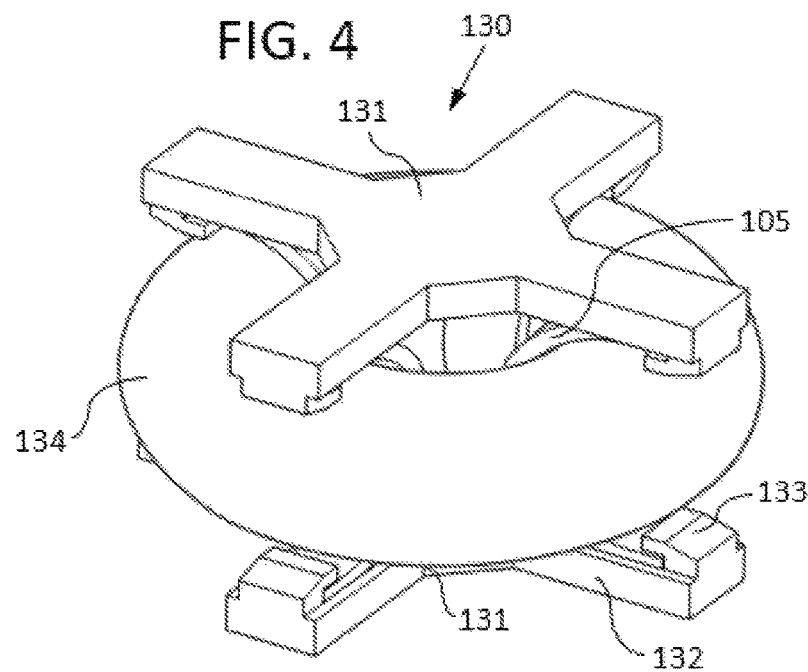

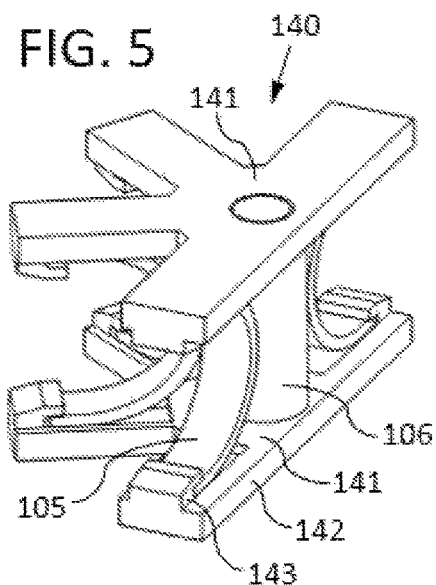
FIG. 5
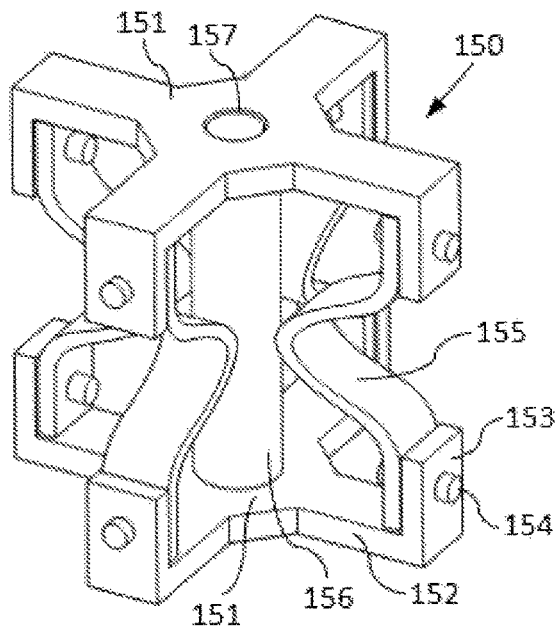
FIG. 6-A
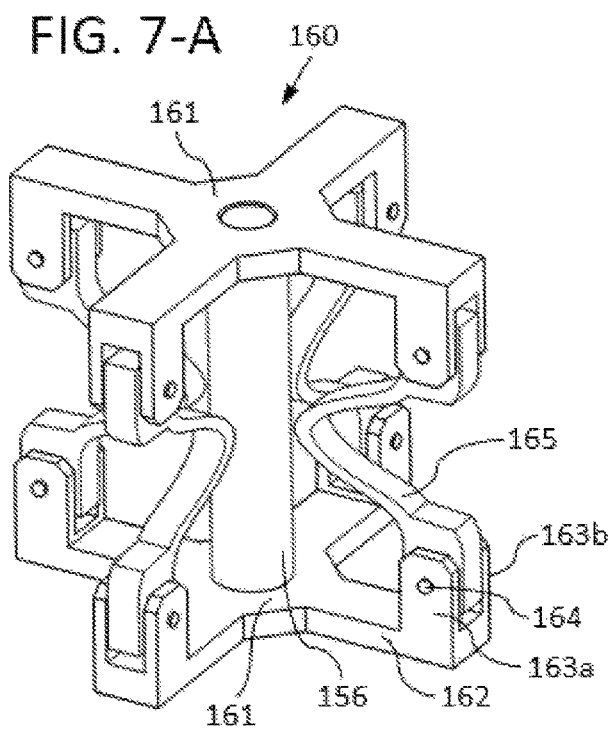
FIG. 7-A
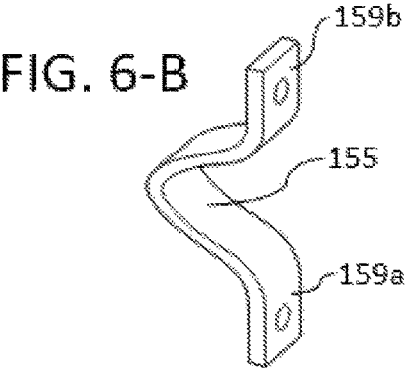
FIG. 6-B
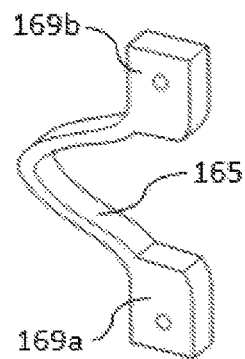
FIG. 7-B

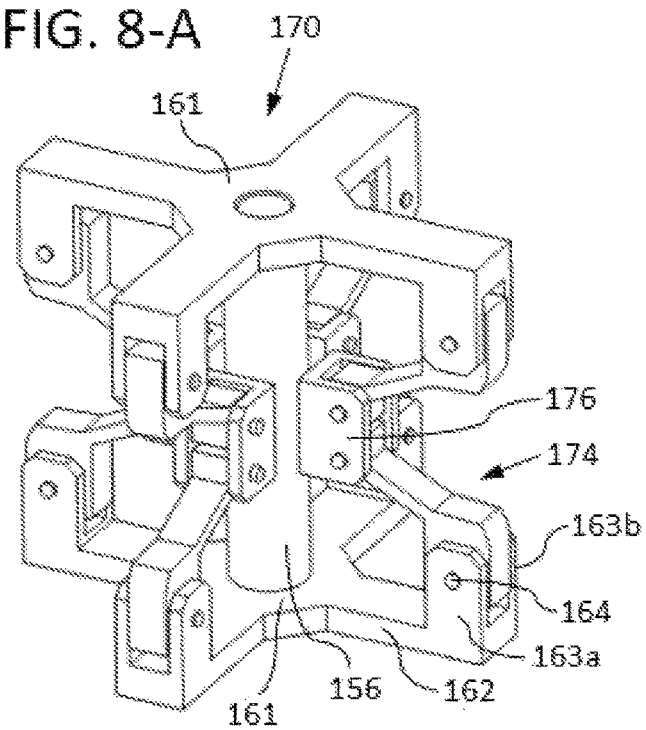
FIG. 8-A
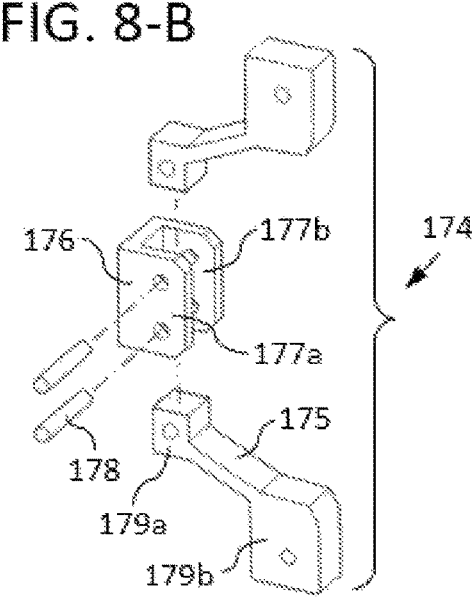
FIG. 8-B
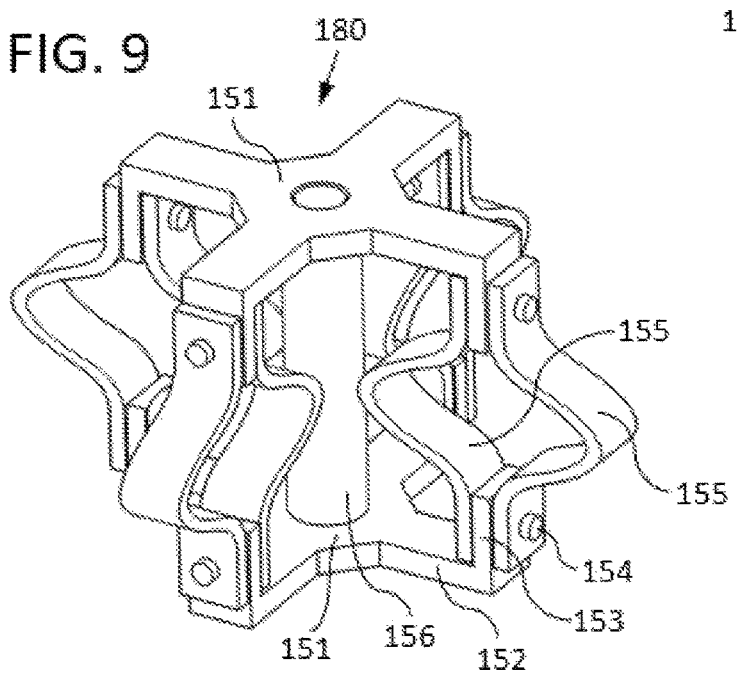
FIG. 9

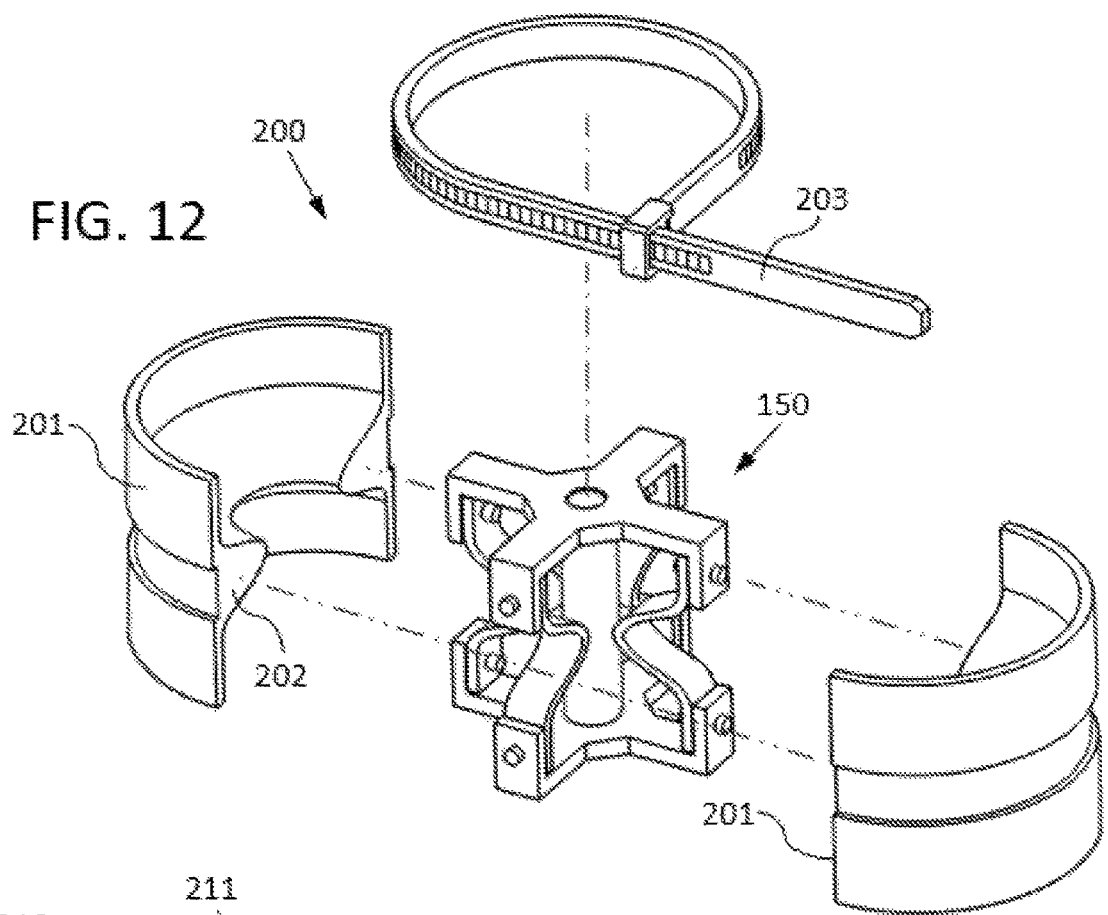
FIG. 12
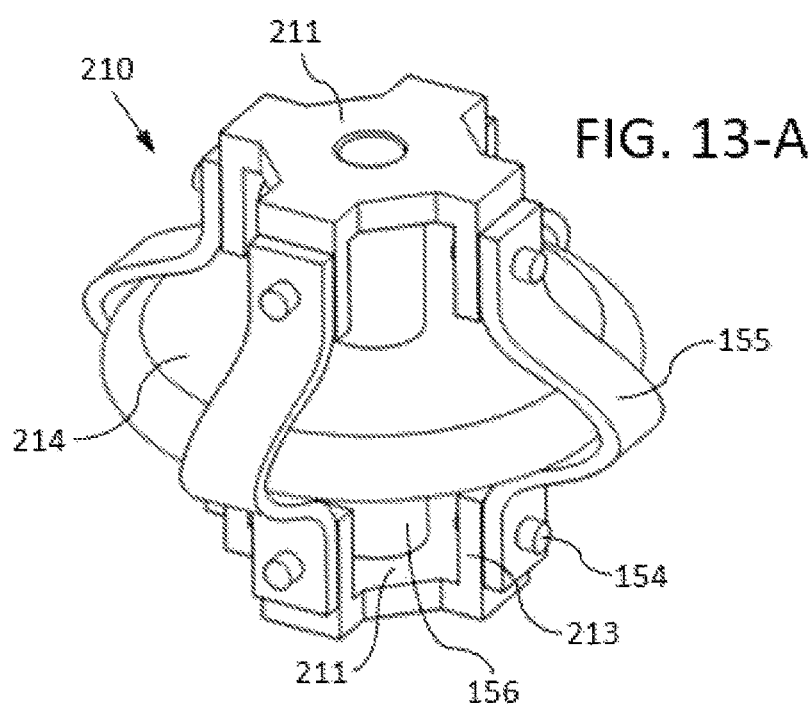
FIG. 13-A

FIG. 13-B

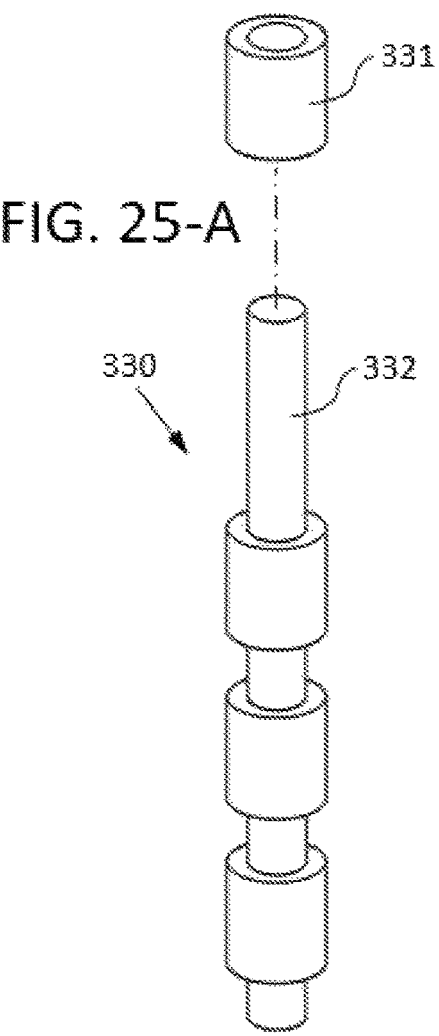
FIG. 25-A
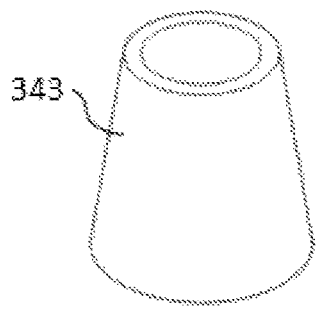
FIG. 25-B
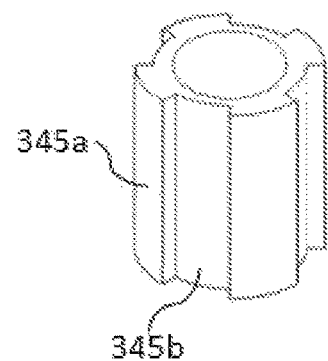
FIG. 25-C
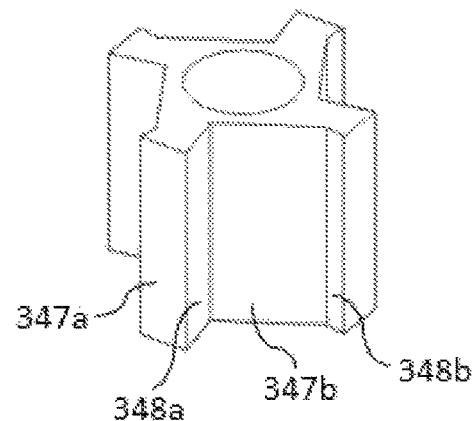
FIG. 25-D

FLEXIBLE STRUCTURE, PARTICULARLY FOR APPLICATIONS IN ROBOTICS AND ORTHOPEDICS

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

Field of Invention

Embodiments of this invention relate to flexible support structures for use in the fields of robotics, orthopedic braces, and structural engineering. More particularly, embodiments of this invention relate to structures that exhibit axial, bending, and twisting flexibility, and possess impact load dampening characteristics.

Prior Art

Many joint assemblies exist today which constrain or support a first body with respect to a second body and permit an amount of relative translation and rotation of the bodies when subjected to an applied load. This has typically been achieved through the use of rigid members and pin joints, and helical springs if restoring forces are required. However, such assemblies typically sacrifice overall strength in order to achieve higher degrees of freedom, and comprise multiple parts. Engineers have sought to overcome these limitations by developing flexible structures with no pin joints, comprising resilient members which are stiff enough to provide support for an unloaded structure, yet can deform a relatively large amount when subjected to moderate loading conditions.

Examples of such flexible structures are shown U.S. Patent Application US 2006/0156851 (Jacobsen et al.), U.S. Pat. No. 10,677,307 (Aagaard et al.), U.S. Pat. No. 8,708, 593 (Stratton). These embodiments successfully employ resilient members to achieve deformations required of the intended applications, yet still have reasonable impact strengths due to the ability of the resilient members to absorb strain energy. However, in each of the embodiments the resilient members can deform past their elastic or fracture limits when subjected to overload conditions, resulting in component damage. Embodiments of the present invention overcome this limitation by combining resilient members with one or more elastomeric members which are sized to interact with and stiffen the structure as the resilient members approach their elastic or fracture limits, thereby increasing the overall integrity of the structure.

Objects and Advantages

Accordingly, several objects and advantages of the present invention are:
(a.) to provide a flexible structure that exhibits axial, bending, and twisting flexibility;
(b.) to provide a flexible structure that possesses axial, bending, and twisting restoring forces;
(c.) to provide a flexible structure that can dampen the effects of impact loads;
(d.) to provide a flexible structure with resilient members that do not break when the flexible structure is subjected to relatively large axial, bending, and twisting loads;
(e.) to provide a flexible structure that is simple and inexpensive to manufacture;

Further objects and advantages will become apparent from a consideration of the ensuing description and drawings.

SUMMARY

In accordance with the present invention, a flexible structure comprises two or more formers, a plurality of resilient members supporting and affixed to the perimeters of the formers, and either an elastomeric central member located between each former and in the center of the resilient members, or an elastomeric surrounding member located between each former and around the resilient members, or both. This construction provides a high strength structure that exhibits axial, bending, and twisting flexibility, and possesses impact load dampening characteristics.

DRAWINGS—FIGURES

FIG. 1-A is a top isometric view of the preferred embodiment of the flexible structure in accordance with the present invention;

FIG. 1-B is a top isometric exploded view of the embodiment shown in FIG. 1-A;

FIG. 2-A is a top isometric view of an alternate central member featuring enlarged sections;

FIG. 2-B is a top isometric view of an alternate central member featuring a sloped surface;

FIG. 2-C is a top isometric view of an alternate central member featuring grooves;

FIG. 2-D is a top isometric view of an alternate central member featuring angled grooves;

FIG. 3 is a top isometric view of an alternate embodiment featuring a varied quantity of resilient members;

FIG. 4 is a top isometric view of an alternate embodiment featuring a toroid surrounding the resilient members;

FIG. 5 is a top isometric view of an alternate embodiment featuring a different orientation of the resilient members;

Figure 10:
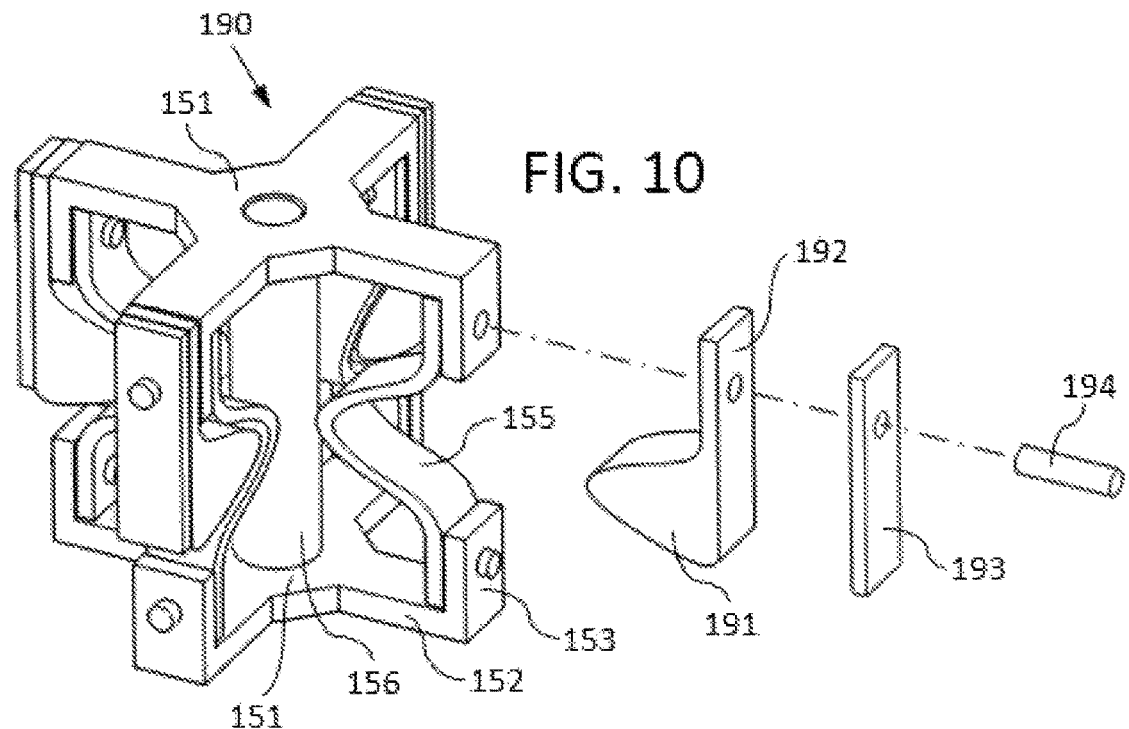
Figure 11:
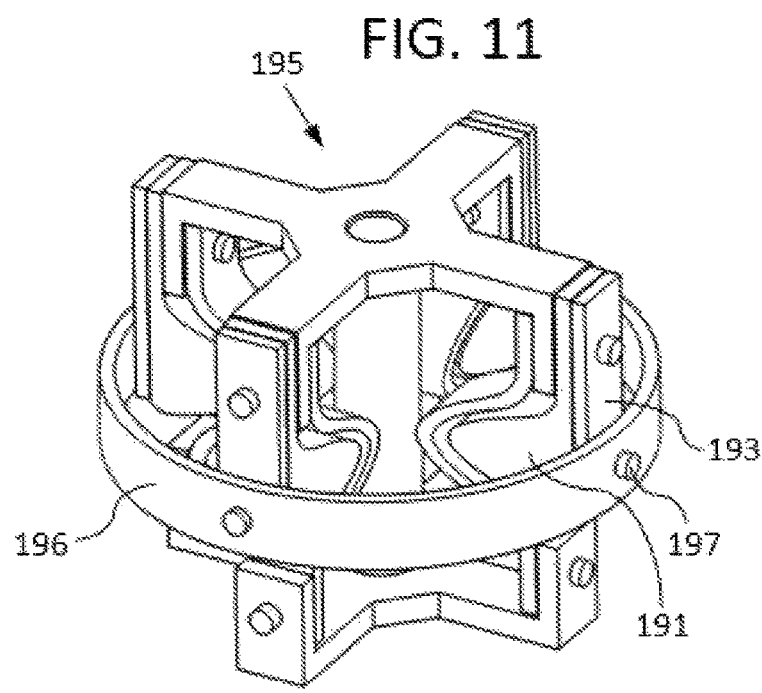
Figure 13:
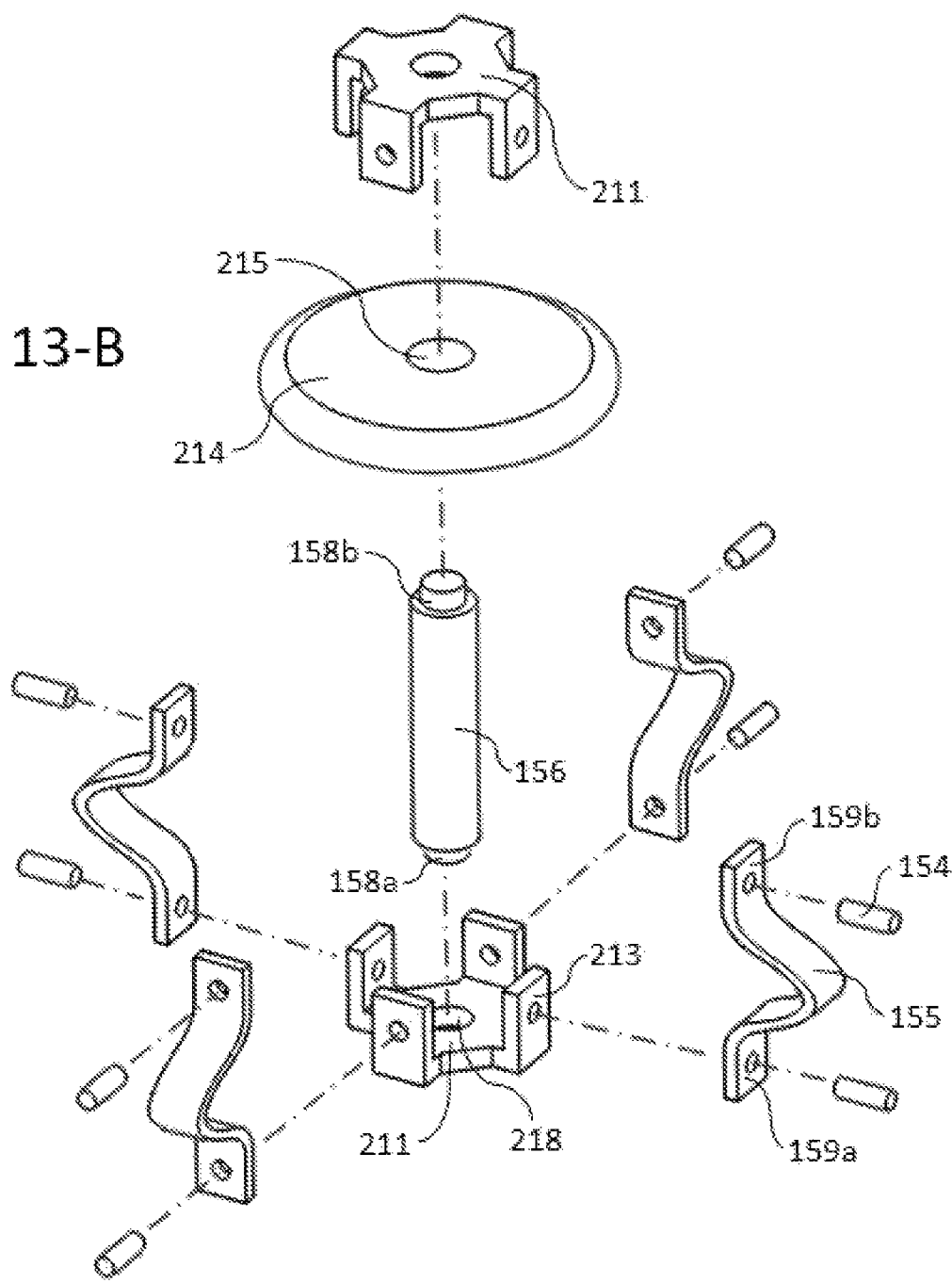
Figure 14:
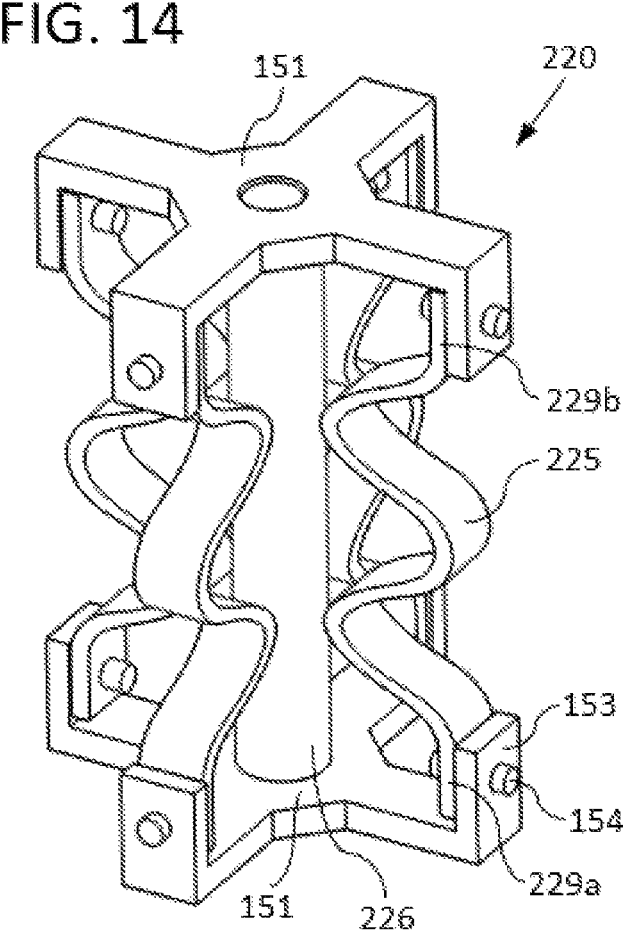
Figure 15:
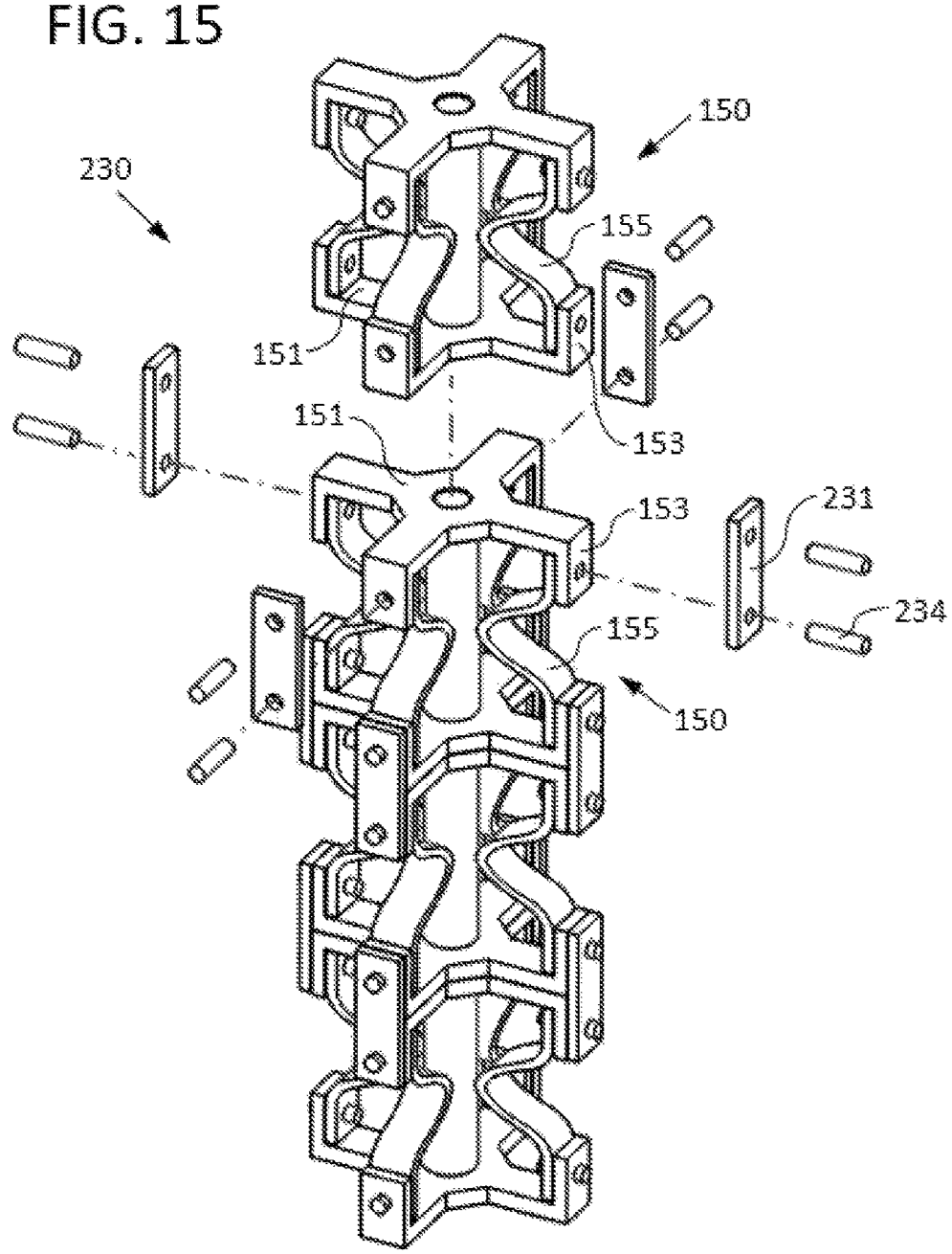
Figure 16:
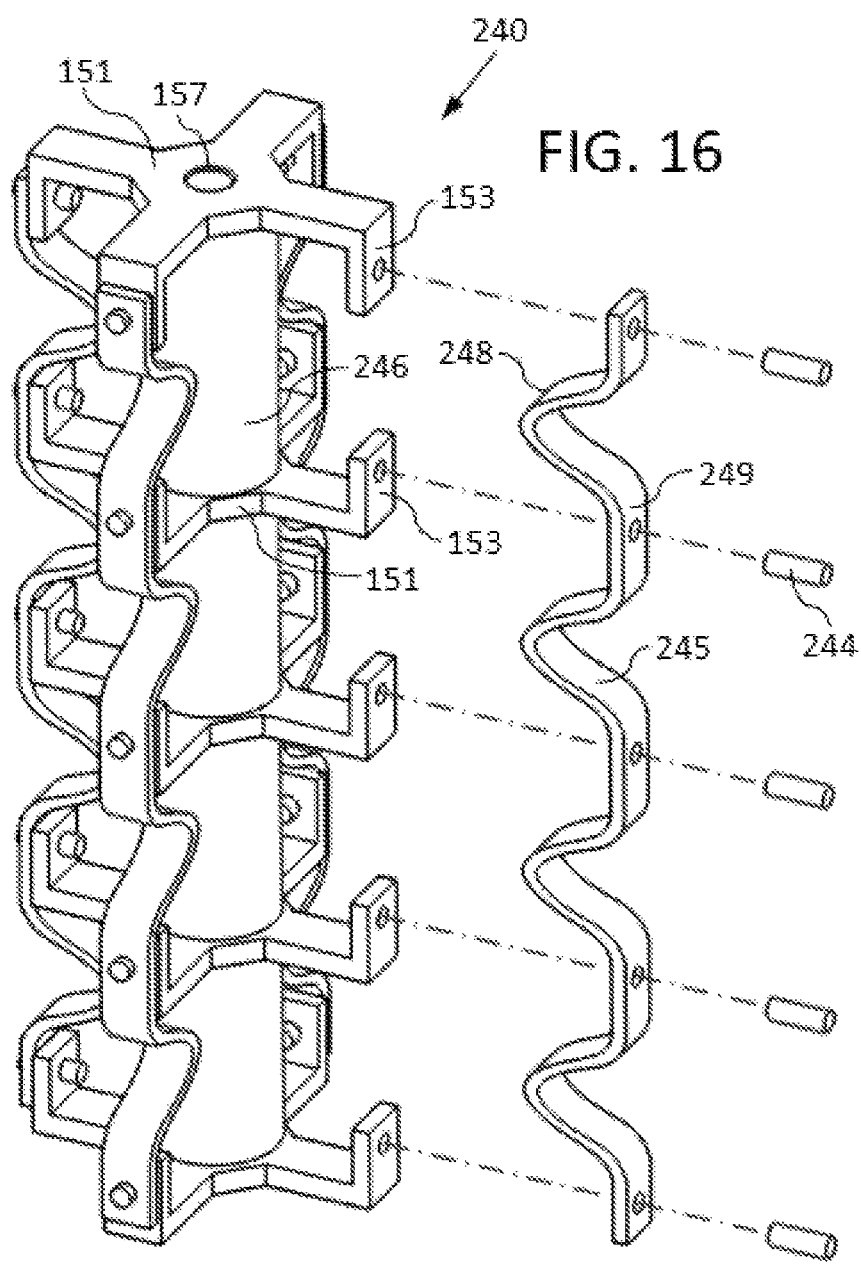
Figure 17:
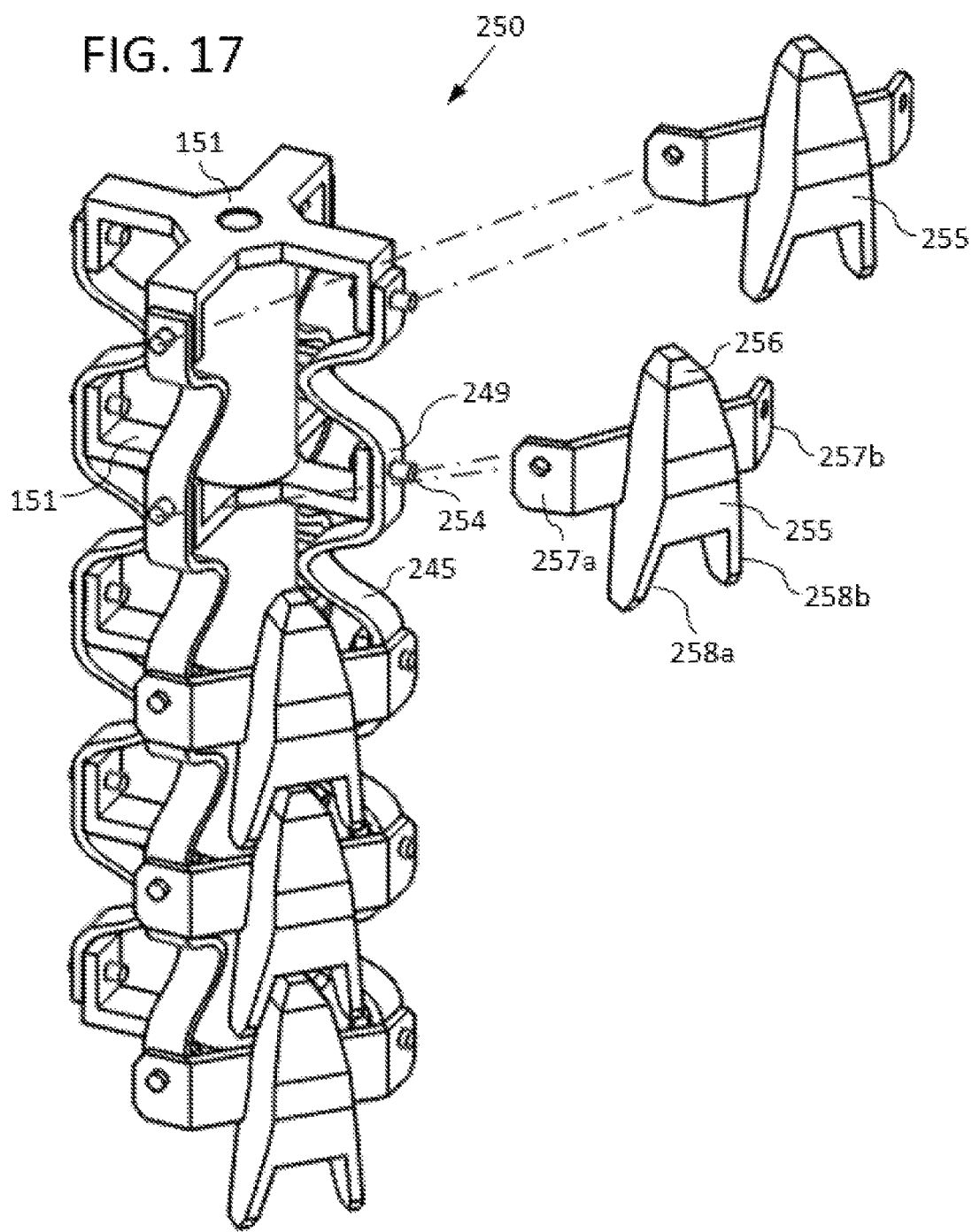
Figure 18:
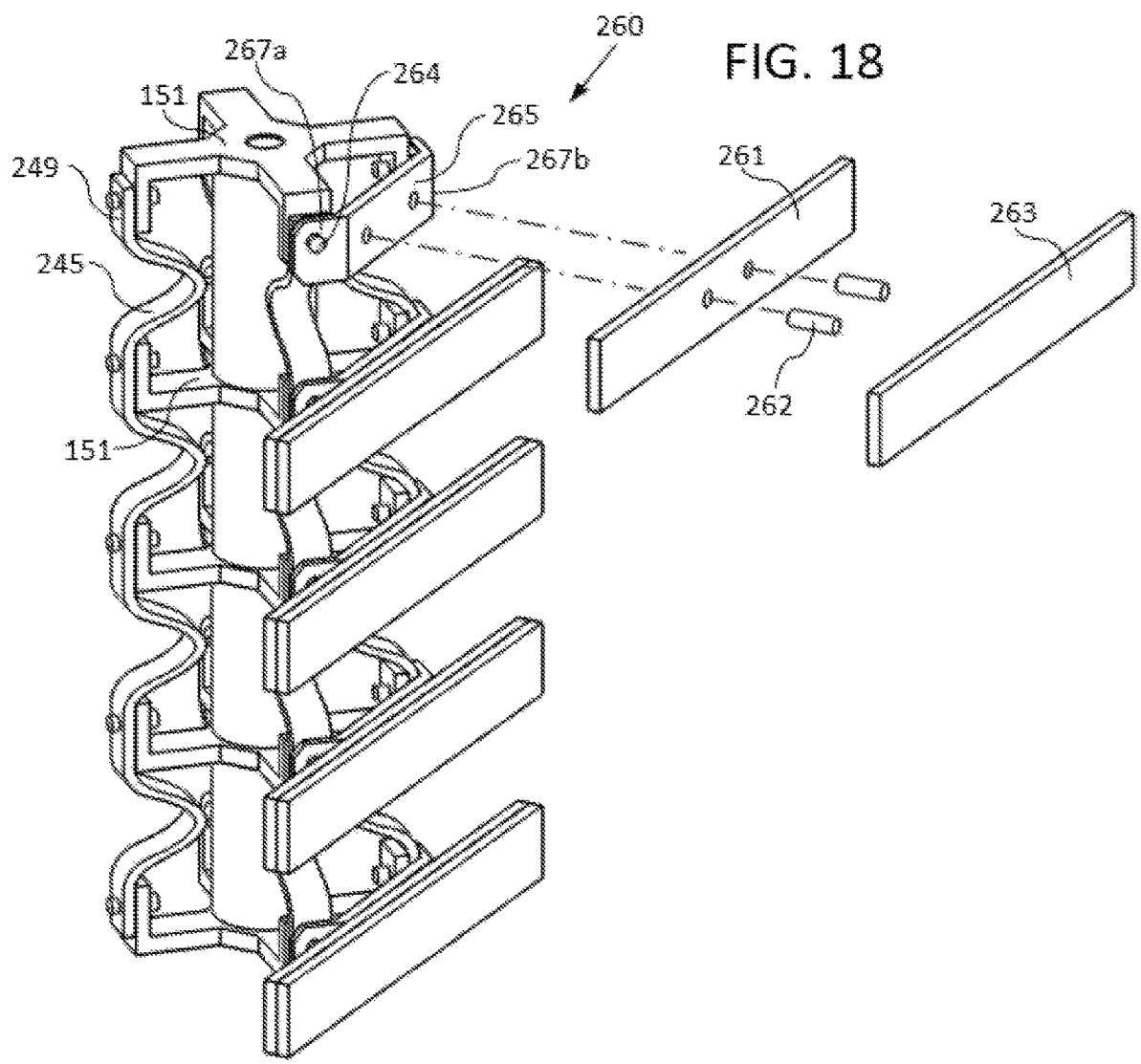
Figure 19:
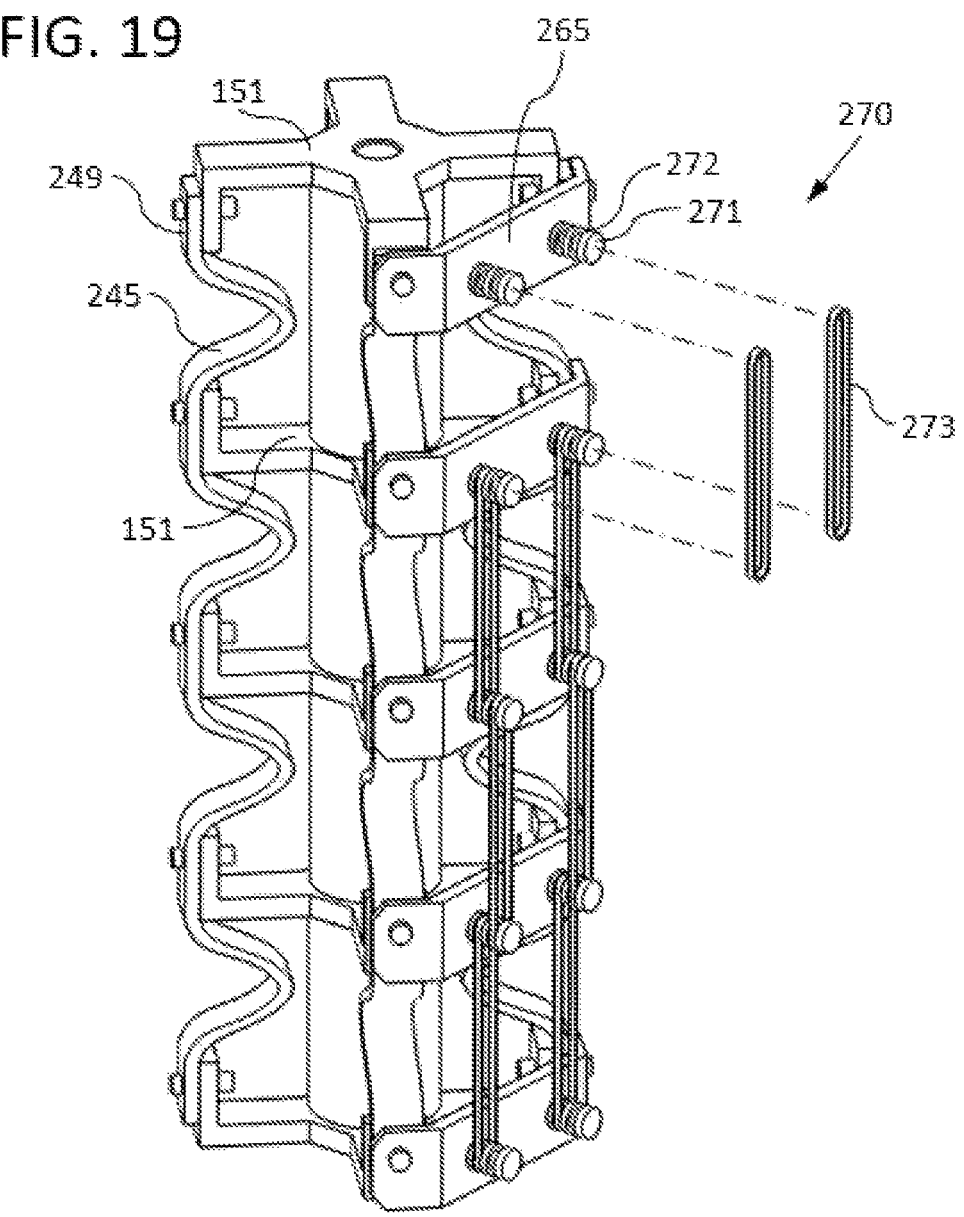
Figure 20:
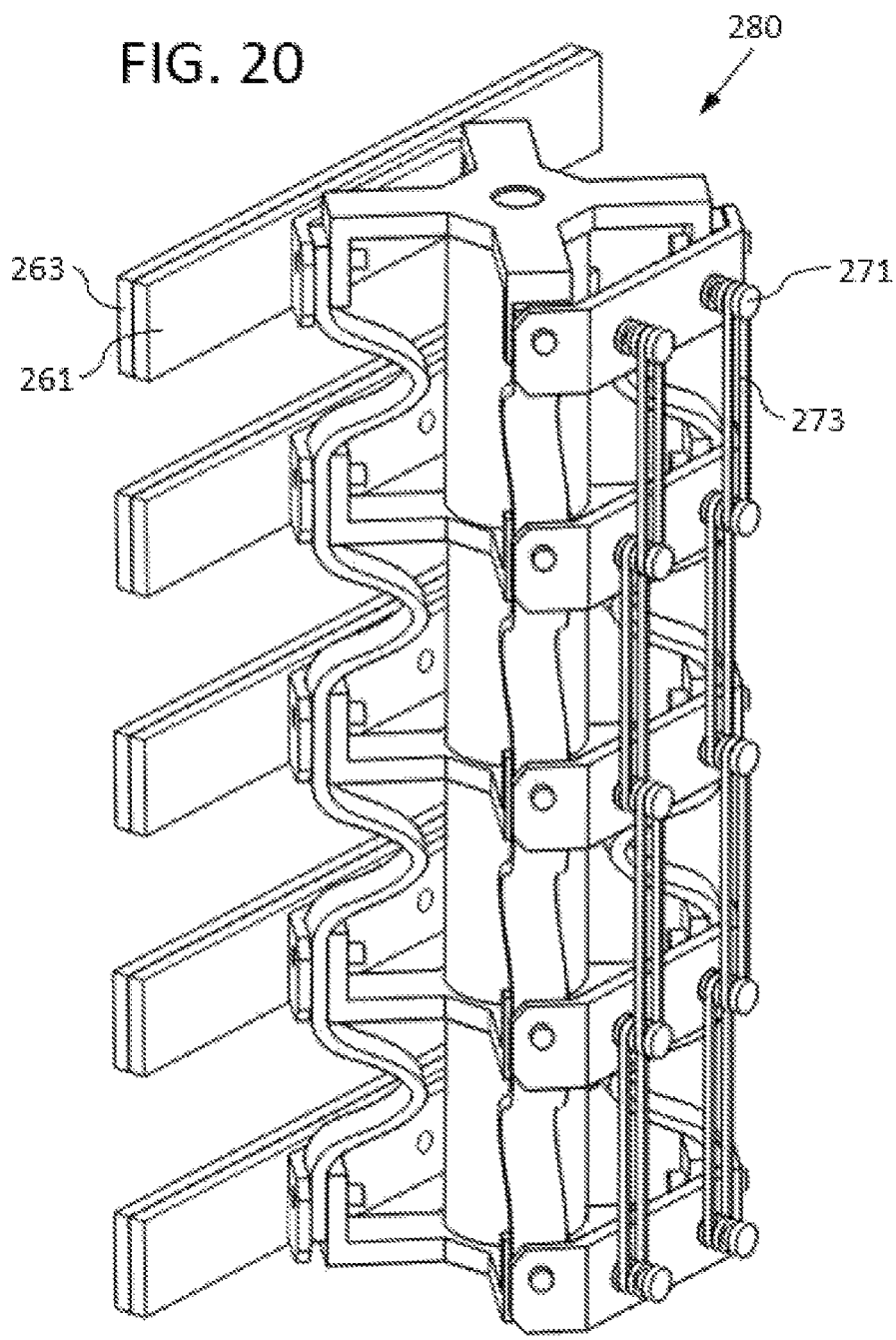
Figure 21:
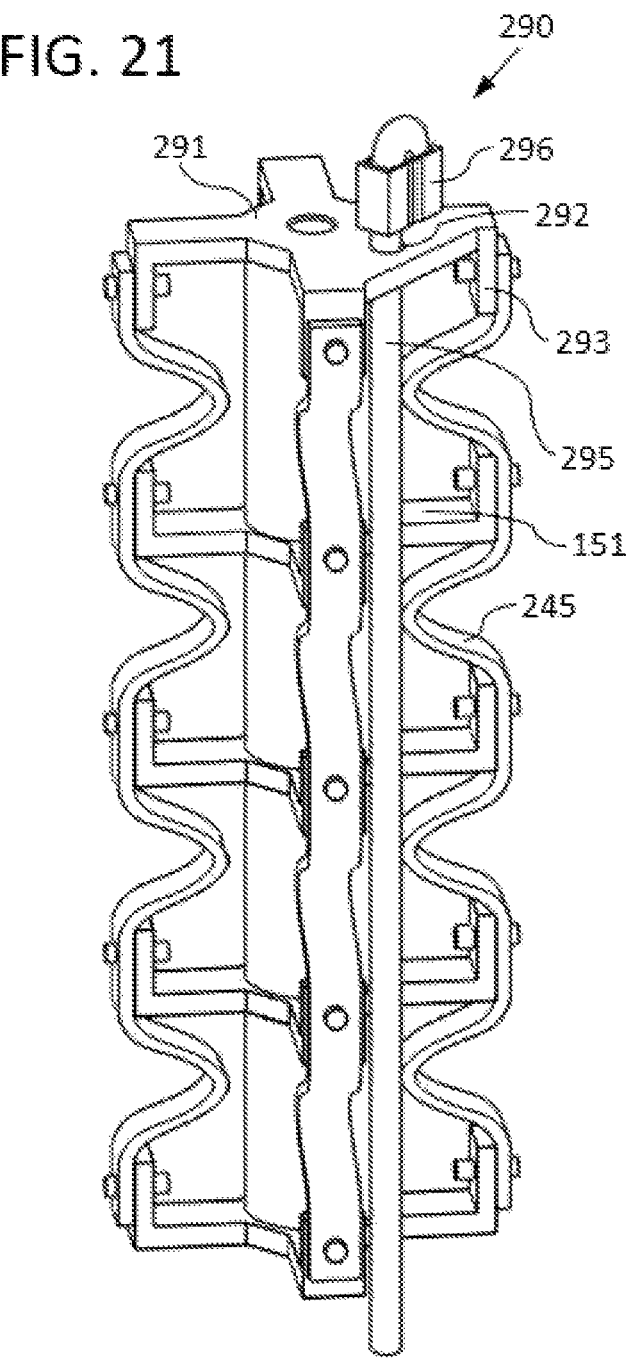
Figure 22:
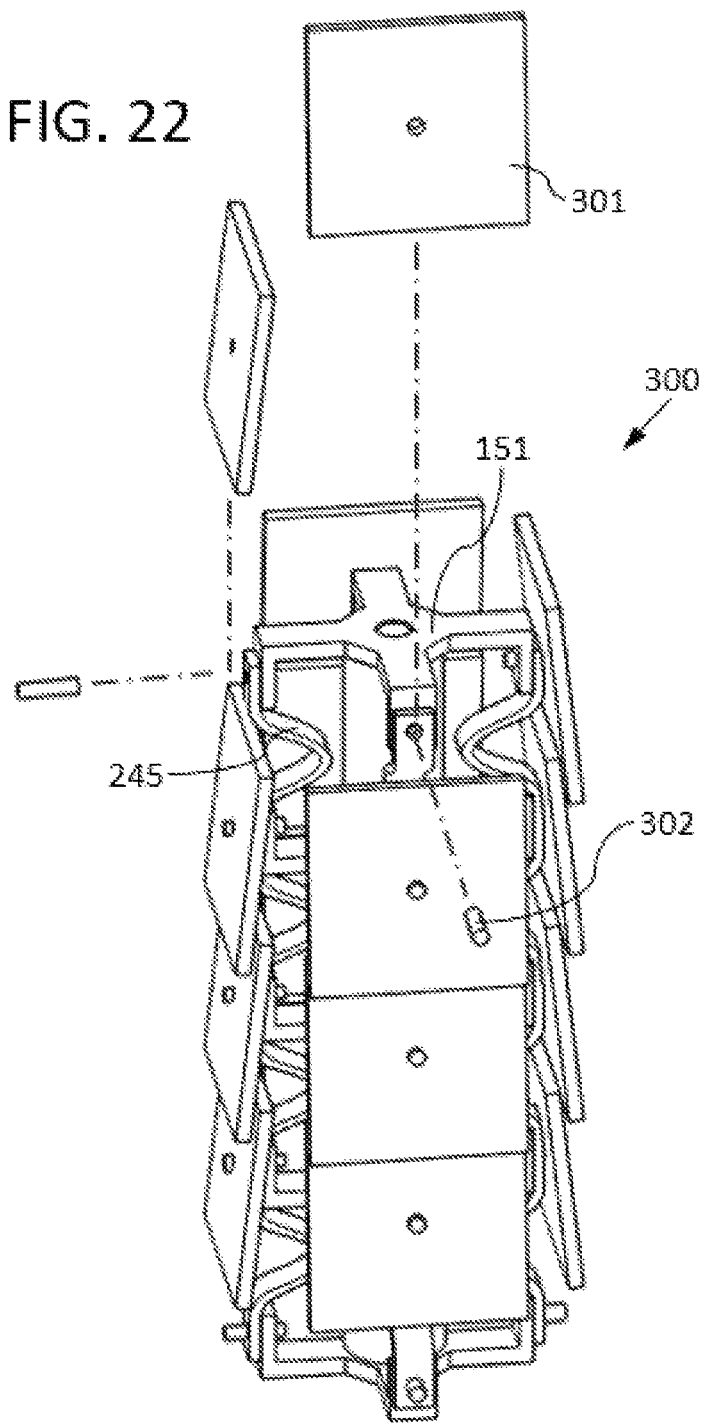
Figure 23:
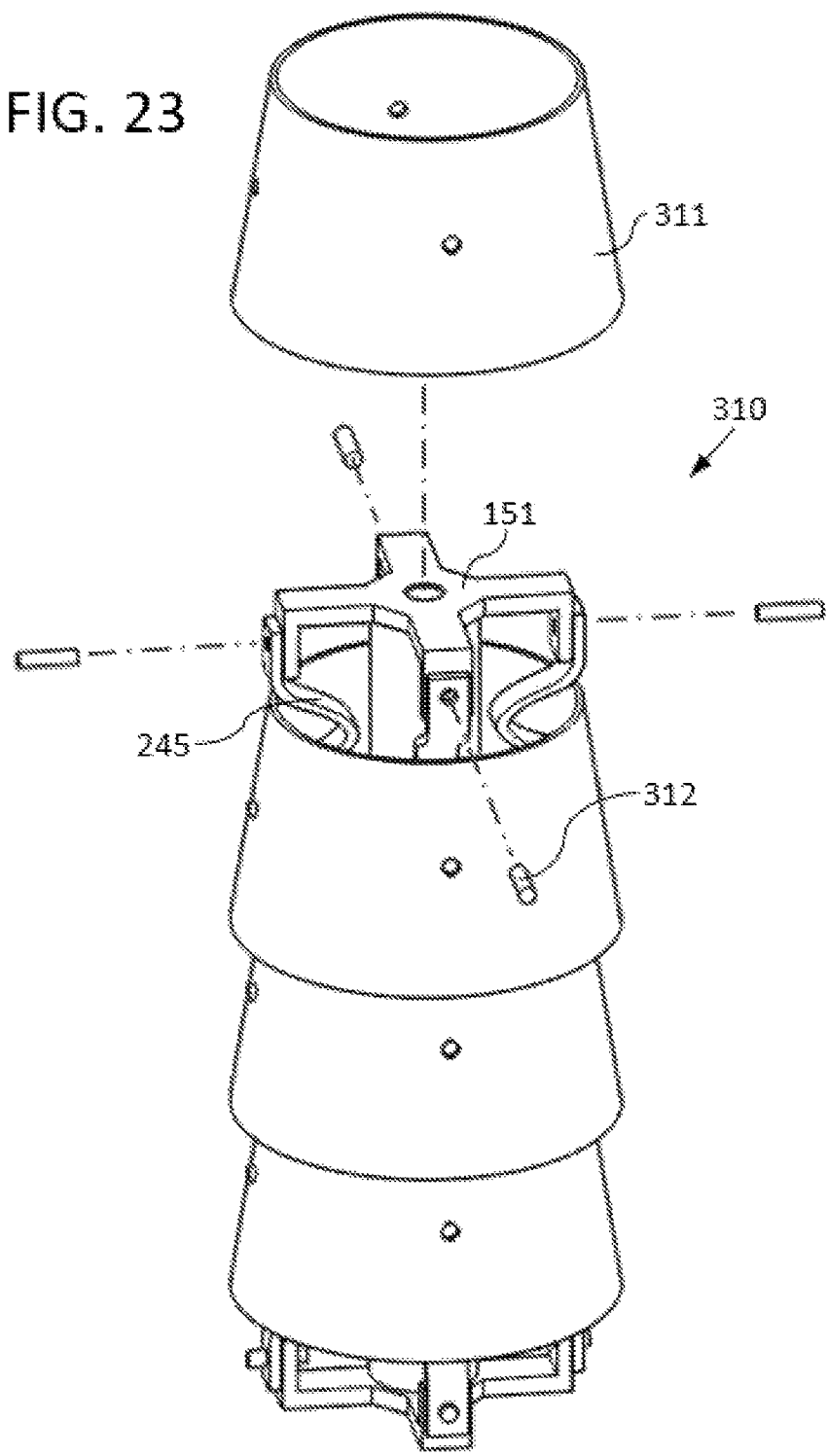
Figure 24:
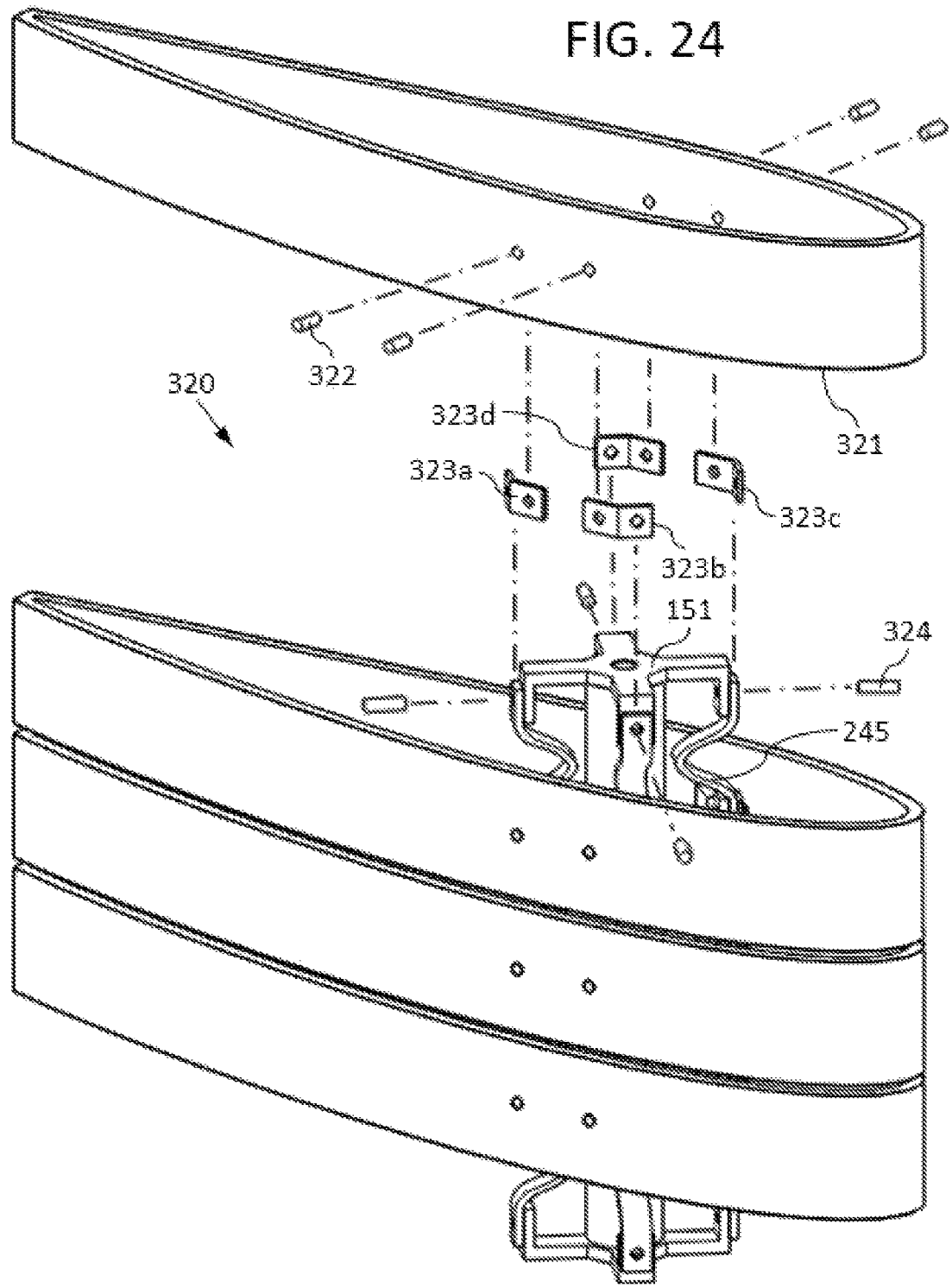

FIG. 6-A is a top isometric view of an alternate embodiment featuring resilient members that have a different shape;

FIG. 6-B is a top isometric detail view of a resilient member of the embodiment shown in FIG. 6-A;

FIG. 7-A is a top isometric view of an alternate embodiment featuring a hinge joint on the ends of the resilient members;

FIG. 7-B is a top isometric detail view of a resilient member of the embodiment shown in FIG. 7-A;

FIG. 8-A is a top isometric view of an alternate embodiment featuring hinged boots;

FIG. 8-B is a top isometric exploded view of a hinged boot of the embodiment shown in FIG. 8-A;

FIG. 9 is a top isometric view of an alternate embodiment featuring additional resilient members;

FIG. 10 is a top isometric exploded view of an alternate embodiment featuring bumpers;

FIG. 11 is a top isometric view of an alternate embodiment featuring an annular ring;

FIG. 12 is a top isometric exploded view of an alternate embodiment featuring a casing;

FIG. 13-A is a top isometric view of an alternate embodiment featuring a different orientation of the resilient members and an internal disk;

FIG. 13-B is a top isometric exploded view of the embodiment shown in FIG. 13-A;

FIG. 14 is a top isometric view of an alternate embodiment featuring resilient members having multiple bends;

FIG. 15 is a top isometric exploded view of an alternate embodiment featuring a plurality of formers and resilient members affixed in a longitudinal arrangement;

FIG. 16 is a top isometric exploded view of an alternate embodiment featuring extended resilient members;

FIG. 17 is a top isometric exploded view of an alternate embodiment featuring multiple elements affixed to the flexible structure such to prevent torsion;

FIG. 18 is a top isometric exploded view of an alternate embodiment featuring multiple lateral members affixed to the flexible structure;

FIG. 19 is a top isometric exploded view of an alternate embodiment featuring elastic bands;

FIG. 20 is a top isometric view of an alternate embodiment featuring a combination of lateral members and elastic bands;

FIG. 21 is a top isometric view of an alternate embodiment featuring a control cable;

FIG. 22 is a top isometric view of an alternate embodiment featuring protective plates;

FIG. 23 is a top isometric view of an alternate embodiment featuring protective shells;

FIG. 24 is a top isometric view of an alternate embodiment featuring airfoil shells;

FIG. 25-A is a top isometric view of an alternate central member featuring slip-on sleeves;

FIG. 25-B is a top isometric view of an alternate slip-on sleeve featuring a sloped surface;

FIG. 25-C is a top isometric view of an alternate slip-on sleeve featuring grooves;

FIG. 25-D is a top isometric view of an alternate slip-on sleeve featuring angled grooves;

REFERENCE NUMERALS

100—Preferred Embodiment
101—Former
102—Arm
103—Flange
104—Recess
105—Resilient Member
106—Central Member
107a—End
107b—End
108—Hole
110—Alternate Central Member
111a—Enlarged Section
111b—Enlarged Section
112a—End
112b—End
113—Alternate Central Member
114a—End
114b—End
115a—Alternate Central Member
115b—Groove
116a—End
116b—End
117a—Alternate Central Member
117b—Angled Groove
118a—Wall
118b—Wall
119a—End
119b—End
120—Alternate Embodiment
121—Former
122—Arm
123—Flange
130—Alternate Embodiment
131—Former
132—Arm
133—Flange
134—Toroid
140—Alternate Embodiment
141—Former
142—Arm
143—Flange
150—Alternate Embodiment
151—Former
152—Arm
153—Flange
154—Rivet
155—Resilient Member
156—Central Member
157—Hole
158a—End
158b—End
159a—Flange
159b—Flange
160—Alternate Embodiment
161—Former
162—Arm
163a—Flange
163b—Flange
164—Pin
165—Resilient Member
169a—End
169b—End
170—Alternate Embodiment
174—Linkage Assembly
175—Member
176—Boot
177a—Wall
177b—Wall
178—Pin
179a—End
179b—End
180—Alternate Embodiment
190—Alternate Embodiment
191—Bumper
192—Flange
193—Member
194—Rivet
195—Alternate Embodiment
196—Ring
197—Rivets
200—Alternate Embodiment
201—Semi-casing
202—Protrusion
203—Strap
210—Alternate Embodiment
211—Former
213—Flange
214—Disk
215—Hole
218—Hole 220—Alternate Embodiment
225—Resilient Member
226—Central Member
229a—Flange
229b—Flange
230—Alternate Embodiment
231—Splice Plate
234—Rivet
240—Alternate Embodiment
244—Rivet
245—Extended Resilient Member
246—Central Member
248—Bend
249—Flat Portion
250—Alternate Embodiment
254—Rivet
255—Element
256—Nose
257a—Tab
257b—Tab
258a—Wall
258b—Wall
260—Alternate Embodiment
261—Lateral Member
262—Rivet
263—Pad
264—Rivet
265—Element
267a—Tab
267b—Tab
270—Alternate Embodiment
271—Standoff
272—Groove
273—Elastic Band
280—Alternate Embodiment
290—Alternate Embodiment
291—Former
292—Hole
293—Flange
295—Cable
296—Crimp Sleeve
300—Alternate Embodiment
301—Plate
302—Rivet
310—Alternate Embodiment
311—Shell
312—Rivet
320—Alternate Embodiment
321—Shell
322—Rivet
323a—Bracket
323b—Bracket
323c—Bracket
323d—Bracket
324—Rivet
330—Alternate Central Structure
331—Sleeve
332—Cylinder
343—Alternate Sleeve
345a—Alternate Sleeve
345b—Groove
347a—Alternate Sleeve
347b—Angled Groove
348a—Wall
348b—Wall

DETAILED DESCRIPTION

Preferred Embodiment-FIG. 1-A, FIG. 1-B

FIG. 1-A and FIG. 1-B show a preferred embodiment 100 of the flexible structure in accordance with the present invention. Preferred embodiment 100 comprises four resilient members 105, a central member 106, and two formers 101.

Formers 101 are preferably machined metal. Each former has four arms 102 extending radially outwards to accommodate resilient members 105. The resilient members are preferably manufactured from bent sheet metal and are only a few inches in length. However, resilient members 105 and formers 101 can be manufactured to have different dimensions on a much smaller or larger scale, and can also be made from other materials such as plastic, wood, or composites. As shown in exploded view FIG. 1-B, arms 102 of formers 101 each comprise a recess 104 and a flange 103, and are preferably sized to accept and secure the ends of resilient member 105 with an interference fit, but can also be sized to have a clearance fit. Each former 101 also has a hole 108. Central member 106 is manufactured from an elastomeric material such to possess axial and bending compliance, and preferably has a circular cross section, however, the cross section can vary in other embodiments. Central member 106 has ends 107a, 107b of reduced diameter that are sized to be inserted into hole 108 of each former 101.

Resilient members 105, central member 106, and formers 101 are interconnected as shown in exploded view FIG. 1-B. Formers 101 are vertically opposed and sandwich central member 106 and resilient members 105. Each resilient member 105 is oriented such that the concavity faces radially outwards with respect to central member 106, and the ends of resilient members 105 are inserted between recesses 104 and flanges 103 of formers 101, thereby creating a flexible structure.

Note that in preferred embodiment 100 formers 101 are cross-shaped, each having four arms 102 extending outwards. However, the shape of formers 101 should not be construed as a limitation. For example, in other embodiments the formers can be rectangularly shaped or disc shaped. Also, note that in preferred embodiment 100 each former 101 features hole 108 to accommodate insertion of ends 107a, 107b on central member 106. However, in other embodiments hole 108 and ends 107a, 107b can be omitted, and the central member can insecurely be located between the formers. Additionally, the central member can be made hollow, thereby allowing the passage of cables or wires within according to the application of the user. Also, note that in preferred embodiment 100, resilient members 105 are affixed to formers 101 by means of interference fits with flanges 103. However, in other embodiments resilient members 105 can be affixed to the formers by means of welding or fasteners. In addition, each resilient member 105 can be layered with one or more additional resilient members 105 such that each arm 102 of formers 101 is supported by two or more resilient members, thereby increasing the stiffness and strength of the flexible structure.

Operation

Preferred Embodiment—FIG. 1-A

FIG. 1-A illustrates preferred embodiment 100 of the flexible structure. In operation, mechanical loads can be imposed on the first former 101 and as a result resilient members 105 either compress or expanded to transmit the mechanical loads to the second former 101. The compliance of resilient members 105 dampens the negative effects of high impact loads transmitted between formers 101. The presence of central member 106 increases the stiffness and strength of the flexible structure, and prevents resilient members 105 from deforming beyond elastic limits. As each resilient member 105 is compressed, it butts up against the surface of central member 106 and the internal loads within resilient member 105 are transmitted to central member 106, thereby increasing the stiffness and strength characteristics of the overall flexible structure. This result occurs when the overall flexible structure is subjected to compression or bending loads. The sizing of resilient members 105 and central member 106 can be chosen such that when the flexible structure is at rest and no loads are applied, there is or is not a gap between resilient members 105 and central member 106. The presence or absence of such gaps will result in different overall stiffness profiles of the flexible structure. In other words, resilient members 105 can be designed to deform or not to deform a certain amount before contacting central member 106. Note the flexible structure can resist twisting and tension, but the stopping effect of the interaction of resilient members 105 and central member 106 will not occur. In applications, foreign objects will be in contact with formers 101 according to the field of use. These objects can either be secured to formers 101 be means of welds or fasteners, or left unsecured. Therefore, the shape of formers 101 can vary according to the application and can possess fastener holes and cutouts.

Description

Alternate Embodiments—FIG. 2-A Through FIG. 25-D

The flexible structure of the present invention can comprise alternate central members instead of aforementioned central member 105, as illustrated in FIG. 2-A through 2-D.

FIG. 2-A shows an alternate central member 110. Similar to central member 106 shown in FIG. 1-B, alternate central member 110 comprises ends 112a, 112b, however, unlike central member 106, alternate central member 110 possesses enlarged sections 111a, 111b. These enlarged sections are preferably sized to create a surface contour similar to the surrounding resilient members, such as resilient members 105 shown in FIG. 1-B. This feature results in a more uniform load distribution as the resilient members are compressed and make contact with the central member, therefore increasing the overall strength of the flexible structure.

FIG. 2-B shows another alternate central member 113. Similar to central member 106 shown in FIG. 1-B, alternate central member 113 comprises ends 114a, 114b, however, unlike central member 106, the surface of alternate central member 113 is sloped along the longitudinal axis. This feature enables the flexibility of the overall structure to be controlled by sliding alternate central member 113 between the formers, such as formers 101. Sliding alternate central member 113 alters the cross-sectional area between the resilient members, such as resilient members 105 shown in FIG. 1-B, thereby effecting the amount the resilient members can be compressed.

FIG. 2-C shows another alternate central member 115a. Similar to central member 106 shown in FIG. 1-B, alternate central member 115a comprises ends 116a, 116b, however, unlike central member 106, the surface of alternate central member 115a contains grooves 115b equal to the amount of surrounding resilient members, such as resilient members 105 shown in FIG. 1-B, and are at least as wide as the resilient members. This feature enables the flexibility of the overall structure to be controlled by rotating alternate central member 115a such that grooves 115b either do or do not align with the resilient members. This effects the amount the resilient members can be compressed.

FIG. 2-D shows another alternate central member 117a. Similar to central member 115a shown in FIG. 2-C, alternate central member 117a comprises grooves 117b and ends 119a, 119b, however, unlike central member 115a, the surfaces of grooves 117b are angled and are wider than the surrounding resilient members, such as resilient members 105 shown in FIG. 1-B. This feature enables the flexibility of the overall structure to be controlled by rotating alternate central member 117a such that the resilient members are at an arbitrary position adjacent to the surfaces of grooves 117b. Since the surfaces of the grooves are angled, the amount the resilient members can compress depends on the angular position of alternate central member 117a. Note that walls 118a, 118b exist to surround each resilient member, therefore limiting how much the central member 117a can be rotated.

FIG. 3 shows an alternate embodiment 120. Alternate embodiment 120 is similar to preferred embodiment 100 shown in FIG. 1-A, however, alternate embodiment 120 consists of three resilient members 105 instead of four. Alternate embodiment 120 accommodates the resilient members using formers 121, each having arms 122 and flanges 123 in a similar fashion as formers 101 of preferred embodiment 100. Alternate embodiment 120 illustrates that the flexible structure can possess an arbitrary quantity of resilient members 105, having more or less than the four shown in preferred embodiment 100.

FIG. 4 shows an alternate embodiment 130. Alternate embodiment 130 is similar to preferred embodiment 100 shown in FIG. 1-A, but instead of comprising central member 106, alternate embodiment 130 comprises an elastomeric toroid 134 surrounding resilient members 105. This feature provides similar benefits that central member 106 does in preferred embodiment 100. Toroid 134 increases the stiffness and strength of the flexible structure, and aids in preventing resilient 105 members from deforming beyond an elastic limit. The sizing of toroid 134 can be selected to achieve various stiffness profiles of the flexible structure. Note that in other embodiments the surrounding member is not limited to the geometry of an absolute toroid, but can have deviations in cross-sections and shapes. Note that alternate embodiment 130 comprises formers 131 having arms 132 and flanges 133 similar to formers 101 in preferred embodiment 100, but do no feature holes since a central member is not present. Note that alternate embodiments can comprise both a central member such as central member 106 in preferred embodiment 100, and a surrounding member such as toroid 134, thereby greatly increasing the overall stiffness and strength characteristics of the overall flexible structure.

FIG. 5 shows an alternate embodiment 140. Alternate embodiment 140 is similar to preferred embodiment 100 shown in FIG. 1-A, however, alternate embodiment 140 comprises formers 141 which have arms 142 and flanges 143 that differ in position relative to arms 102 of formers 101 in preferred embodiment 100. Alternate embodiment 140 illustrates that the flexible structure can possess arbitrary positionings of resilient members 105, and is not limited to the positionings shown in preferred embodiment 100.

FIG. 6-A shows an alternate embodiment 150. Alternate embodiment 150 is similar to preferred embodiment 100, however, unlike preferred embodiment 100 alternate embodiment 150 comprises resilient members 155, a central member 156, and formers 151 which each have a hole 157, arms 152, and flanges 153 that project relatively perpendicular to the arms. Arms 152 are sized to accommodate the securing of resilient member 155. FIG. 6-B shows a detail view of one of resilient members 155. Resilient member 155 is a bent member and comprises flanges 159a, 159b. The resilient members are preferably manufactured from sheet metal, however can also be manufactured from other materials such as plastic, wood, or composites. Flanges 159a, 159b are secured to flanges 153 of formers 151 by means rivets 154. Note that in other embodiments more than one rivet 154 can be used at each interface. Also, note that in other embodiments resilient members 155 can be secured to arms 152 by means of pins, screws, or weld joints instead of using rivets 154.

FIG. 7-A shows an alternate embodiment 160. Alternate embodiment 160 is similar to alternate embodiment 150, however, unlike alternate embodiment 150 alternate embodiment 160 comprises resilient members 165 and formers 161 which each have arms 162 and flanges 163a, 163b that project relatively perpendicular to the arms and are sized to accommodate hinge interfaces with resilient members 165. FIG. 7-B shows a detail view of one of resilient members 165. Resilient member 165 is a bent member and comprises ends 169a, 169b. Ends 169a, 169b are secured to flanges 163a, 163b of formers 161 by means pins 164. This feature reduces internal bending stresses in ends 169a, 169b of each resilient member 165 when the flexible structure is subjected to loads.

FIG. 8-A shows an alternate embodiment 170. Alternate embodiment 170 is similar to alternate embodiment 160, however, unlike alternate embodiment 160 alternate embodiment 170 comprises linkage assemblies 174 instead of resilient members 165. FIG. 8-B shows an exploded view of one of linkage assemblies 174 which comprises two members 175 and a boot 176. Ends 179a of members 175 are affixed to flanges 177a, 177b of boot 176 by means of pins 178. Ends 179b of members 175 on each linkage assembly 174 are affixed to flanges 163a, 163b of formers 161 as shown in FIG. 8-A. The presence of the pin joints reduces the internal bending stresses in members 175 when the flexible structure is subjected to loads.

FIG. 9 shows an alternate embodiment 180. Similar to alternate embodiment 150 shown in FIG. 6-A, alternate embodiment 180 comprises formers 151 and resilient members 155. However, unlike alternate embodiment 150, alternate embodiment 180 has two oppositely faced resilient members 155 affixed to each arm 152 on each former 151 instead of just one. The presence of the additional resilient member 155 affixed to each arm 152 increases the overall strength and stiffness of the flexible structure.

FIG. 10 shows an alternate embodiment 190. Similar to alternate embodiment 150 shown in FIG. 6-A, alternate embodiment 190 comprises formers 151 and resilient members 155. However, alternate embodiment 190 further comprises bumpers 191. Each bumper 191 has a flange 192 and is affixed to one of flanges 153 of one of formers 151 preferably by means of at least one rivet 194. Bumpers 191 are preferably manufactured from an elastomeric material, but can also be made of a stiffer material such as metal, plastic, or wood. Bumpers 191 are shaped to make contact with either the surface of resilient members 155 or a portion of the opposite former 151 to which the bumpers are affixed to. If bumpers 191 are manufactured from an elastomeric material, a member 193 is preferably affixed to the outside surface of each bumper 191 by an adhesive means, thereby providing extra stiffness to the bumper. The bumpers give the flexible structure additional stiffness and strength and prevent each resilient member 155 from be compressed beyond elastic limits.

FIG. 11 shows an alternate embodiment 195. Alternate embodiment 195 is similar to alternate embodiment 190 shown in FIG. 10, however alternate embodiment 195 further comprises a ring 196. Preferably, each bumper 191 is manufactured as an elastomeric material and is adhered to member 193, and ring 196 is affixed to each member 193 by means of rivets 197. Note that in other embodiments, ring 196 can instead be welded to members 193, or the members can be machined into the geometry of ring 196. Also, if bumpers 191 are manufactured as a stiff material such as metal, plastic, or wood, then members 193 can be omitted and ring 196 can be directly affixed to bumpers 191. The presence of ring 196 provides stability to bumpers 191.

FIG. 12 shows an alternate embodiment 200. Alternate embodiment 200 is similar to alternate embodiment 150 but further comprises two semi-casings 201 enveloping the remaining structure. The semi-casings are preferably manufactured as an elastomeric material, however can also be manufactured out of metal, plastic, or wood. The semi-casings comprise a shell with a protrusion 202 along the interior surface. The protrusion is sized to fit within the bend of the resilient members such as resilient member 155, which adds stiffness and strength to the flexible structure and prevents the resilient members from being compressed beyond elastic limits. Semi-casings 201 can be secured together using a strap 203, however, in other embodiments the semi-casings can be secured together using an adhesive means, or the semi-casings can have holes such that the semi-casings can be secured together using nut and bolt hardware. In addition to providing structural characteristics to the flexible structure, the presence of semi-casings 201 also protects the flexible structure from foreign object debris.

FIG. 13-A shows an alternate embodiment 210. Similar to alternate embodiment 150 shown in FIG. 6-A, alternate embodiment 210 comprises formers 211 and resilient members 155. However, unlike alternate embodiment 150, resilient members 155 of alternate embodiment 210 are oriented such that the concavities face inward rather outward, and further comprises a disk 214 sized to fit within the concavities of resilient members 155. As shown in exploded view FIG. 13-B, disk 214 preferably has a hole 215 and central member 156 exists so that the disk can be slid on the central member with a friction fit. Formers 211 each have a hole 218 and flanges 213 to accommodate resilient members 155 and central member 156 in a similar fashion as alternate embodiment 150. Disk 214 is preferably manufactured from an elastomeric material, however can also be manufactured out of metal, plastic, or wood. Note that in other embodiments central member 156 can be omitted. The presence of disk 214 provides the flexible structure with additional stiffness and strength, and prevents each resilient member 155 from being compressed beyond elastic limits.

FIG. 14 shows an alternate embodiment 220. Similar to alternate embodiment 150 shown in FIG. 6-A, alternate embodiment 220 comprises formers 151 and a central member 226. However, unlike alternate embodiment 150, resilient members 225 of alternate embodiment 220 comprise multiple bends. Resilient members 225 are affixed to formers 151 in a similar fashion as the resilient members in alternate embodiment 150. Flanges 229a, 229b are preferably affixed to flanges 153 of formers 151 by means of rivets 154. Resilient members 225 are more compliant than resilient members 155 shown in FIG. 6-A, thereby allowing the flexible structure to deform a greater amount before breaking. Note that in other embodiments, toroids can be located around the bends of resilient members 225, such as toroid 134 as illustrated in FIG. 4.

FIG. 15 shows an alternate embodiment 230 having a plurality of the flexible structures of alternate embodiment 150 shown in FIG. 6-A that are arranged in a longitudinal manner. Formers 151 of each alternate embodiment 150 are vertically opposed with the formers of an adjacent alternate embodiment 150, and flanges 153 of the formers are secured together preferably by splice plates 231 and a fastening means such as rivets 234. Note that in other embodiments splice plates 231 can be omitted, and formers 151 can be secured directly together by an adhesive, welding, or fasting means. Also, the two back-to-back formers 151 can be manufactured as one piece. The multitude of resilient members 155 of alternate embodiment 230 contribute to a longitudinal structure that exhibits low stiffness and high strength characteristics. Note that alternate embodiment 230 is not limited to constituent alternate embodiments 150, but can comprise an assembly of other alternate embodiments mentioned heretofore in this specification.

FIG. 16 shows an alternate embodiment 240. Alternate embodiment 240 is similar to alternate embodiment 230 shown in FIG. 15, comprising formers 151 with holes 157 and central members 246. However, instead of resilient members 155, alternate embodiment 240 comprises extended resilient members 245. Extended resilient members 245 each comprise multiple bends 248 and flat portions 249. The flat portions of resilient members 245 are affixed to flanges 153 of formers 151 by means rivets 244. In other embodiments the extended resilient members 245 can be affixed to flanges 153 by a screw, weld, or adhesive means. Alternate embodiment 240 exhibits the same characteristics as embodiment 230, but has a reduced part count.

FIG. 17 shows an alternate embodiment 250. Alternate embodiment 250 is similar to alternate embodiment 240 shown in FIG. 16, comprising formers 151 and extended resilient members 245. Alternate embodiment 250 further comprises elements 255. Elements 255 are preferably manufactured as a stiff material such as metal, plastic, or wood, however can also be manufactured as or lined with an elastomeric material. Elements 255 comprise tabs 257a, 257b sized so that elements 255 can be affixed to flat portions 249 of extended resilient members 245 preferably by means of rivets 254. In other embodiments elements 255 can be affixed to flat portions 249 of extended resilient members 245 by a screw, weld, or adhesive means. Elements 255 each have a nose 256 manufactured on one end and walls 258a, 258b manufactured on the end opposite nose 256. Nose 256 and walls 258a, 258b are sized such that when elements 255 are affixed to the remaining structure of alternate embodiment 250, nose 256 of one element 255 rests between walls 258a, 258b of the adjacent element 255. This arrangement prevents alternate embodiment 250 from exhibiting excessive bending or twisting that could otherwise cause damage to extended resilient members 245. When nose 256 on one element 255 displaces and makes contact with walls 258a, 258b of an adjacent member 255, alternate embodiment 250 stiffens. Note that in other embodiments, elements 255 can have additional walls oriented perpendicular to walls 258a, 258b, further preventing bending of the flexible structure about all axes.

FIG. 18 shows an alternate embodiment 260. Alternate embodiment 260 is similar to alternate embodiment 240 shown in FIG. 16, comprising formers 151 and extended resilient members 245. Alternate embodiment 260 further comprises elements 265 and lateral members 261, which are preferably manufactured from a stiff material such as metal, plastic, or wood. Each element 265 possesses tabs 267a, 267b and are sized so that elements 265 can be affixed to flat portions 249 of extended resilient members 245 preferably by means of rivets 264. In other embodiments elements 265 can be affixed to flat portions 249 of extended resilient members 245 by a screw, weld, or adhesive means. Lateral members 261 are preferably flat and have a high aspect ratio. Lateral members 261 are affixed to elements 265 preferably by means of rivets 262. In other embodiments lateral members 261 can be affixed to elements 265 by a screw, weld, or adhesive means. A pad 263, preferably made of a soft material such as an elastomer or foam, has the same planform shape as lateral members 261 and is affixed to each lateral member using an adhesive. Note that in other embodiments pads 263 can be omitted, and lateral members 261 can have additional holes or cutouts to accommodate installation of other parts or equipment depending on the application of the user. In addition, the geometry of lateral members 261 can be modified. For example, in robotics the lateral members can be curved to resemble anatomical ribs. Also, in orthopedics the lateral members can be curved to surround body parts such as legs, arms, or fingers, such to act as an orthopedic brace.

FIG. 19 shows an alternate embodiment 270. Alternate embodiment 270 is similar to alternate embodiment 240 shown in FIG. 16, comprising formers 151 and extended resilient members 245. Alternate embodiment 270 further comprises elements 265 affixed to flat portions 249 of extended resilient members 245 in a similar fashion as described in alternate embodiment 260 shown in FIG. 18. One or more standoffs 271 are affixed to each element 265. Each standoff 271 has at least one, preferably two grooves 272 along its circumference and are sized such that elastic bands 273 can be stretched and affixed between standoffs 271 of separate elements 265. This feature enables a user to customize the shape of the flexible structure to match an arbitrary contour by adding one or more elastic bands 273 between certain standoffs 271. Note that in other embodiments a hook or groove feature can be incorporated into either formers 151 or elements 265, which eliminates the need for standoffs 271.

FIG. 20 shows an alternate embodiment 280. Alternate embodiment 280 is similar to alternate embodiment 240 as shown in FIG. 16 and further combines the features present in alternate embodiment 260 as shown in FIG. 18 and alternate embodiment 270 as shown in FIG. 19. Alternate embodiment 280 comprises lateral members 261 and pads 263 affixed to one side of the flexible structure by the means described in alternate embodiment 260. Alternate embodiment 280 also comprises standoffs 271 and elastic bands 273 affixed to the flexible structure, opposite the side securing lateral members 261, by the means described in alternate embodiment 270. The combination of these features can act as an orthopedic brace for human limbs or a human back, which possess organic surface shapes.

FIG. 21 shows an alternate embodiment 290. Alternate embodiment 290 is similar to alternate embodiment 240 as shown in FIG. 16, comprising formers 151 and extended resilient members 245. Alternate embodiment 290 further comprises at least one former 291 and at least one cable 295. Former 291 is similar to formers 151, comprising flanges 293, but also possesses at least one hole 292 such that cable 295 can inserted in. A crimp sleeve 296 is affixed to one end of the cable 295. This feature enables either a human, a mechanism, or an electromechanical device to provide a tension force on cable 295 to create a bending motion on the flexible structure. Note that additional cables 295 can be added to the flexible structure to gain more degrees of freedom.

FIG. 22 shows an alternate embodiment 300. Alternate embodiment 300 is similar to alternate embodiment 240 shown in FIG. 16, comprising formers 151 and extended resilient members 245. Alternate embodiment 300 further comprises plates 301, which are preferably manufactured from a stiff material such as metal, plastic, or wood, and are preferably rectangular in shape. Plates 301 are affixed to the flat portions of extended resilient members 245 preferably by means of rivets 302. Also, note that in other embodiments the plates can be secured directly to the extended resilient members by an adhesive, welding, or screw means. Plates 301 act to protect the internal flexible structure from foreign object debris, as well as to make the surface more streamline.

FIG. 23 shows an alternate embodiment 310. Alternate embodiment 310 is similar to alternate embodiment 240 shown in FIG. 16, comprising formers 151 and extended resilient members 245. Alternate embodiment 310 further comprises shells 311 which are preferably manufactured from a stiff material such as metal, plastic, or wood, and are preferably cylindrical in shape and have a sloped surface. Shells 311 are affixed to the flat portions of extended resilient members 245 preferably by means of rivets 312.

FIG. 24 shows an alternate embodiment 320. Alternate embodiment 320 is similar to alternate embodiment 240 shown in FIG. 16, comprising formers 151 and extended resilient members 245. Alternate embodiment 320 further comprises shells 321, which are preferably manufactured from a stiff material such as metal, plastic, or wood, and are shaped like an airfoil or hydrofoil. Shells 321 are affixed to formers 151 preferably by means of adapter brackets 323a, 323b, 323c, 323d and rivets 322, 324. Also, note that in other embodiments the formers and shells can be secured directly together by an adhesive, welding, or screw means. Shells 321 act to decrease drag and increase lift forces when subjected to fluid flow. Note that in other embodiments each individual shell 321 can be stiffened and strengthened with internal stiffeners and ribs.

FIG. 25-A shows an alternate central structure 330. Alternate central structure 330 is applicable to the embodiments of the current invention shown in FIG. 15 through 24 which comprise multiple formers 151 and resilient members. For example, central members 246 from alternate embodiment 240 shown in FIG. 16 can be substituted with alternate central structure 330 shown in FIG. 25-A. Alternate central structure 330 comprises sleeves 331 and a cylinder 332. Sleeves 331 and cylinder 332 are preferably manufactured from an elastomeric material. Cylinder 332 preferably has a circular cross section and is sized to fit along the length and through the holes of the formers of the flexible structure, such as holes 157 of formers 151 of alternate embodiment 240 shown in FIG. 16. Sleeves 331 are positioned along the length of cylinder 332 and between the formers. Sleeves 331 are preferably affixed to cylinder 332 by an adhesive means, but can also be installed with an interference fit. The presence of alternate central structure 330 reduces the overall part count of the flexible structure. Note that in other embodiments cylinder 332 can be hollow, thereby allowing cables or wires to pass through according to the user's application.

FIG. 25-B shows an alternate sleeve 343 that can be used to replace sleeves 331 in alternate central structure 330 shown in FIG. 25-A. The surface of alternate sleeve 343 is sloped along its longitudinal axis. This feature enables the flexibility of the overall structure to be controlled by shifting cylinder 332 along the length of the flexible structure, effectively altering the cross-sectional area between the resilient members, thereby effecting the amount the resilient members can be compressed.

FIG. 25-C shows an alternate sleeve 345a that can be used to replace sleeves 331 in alternate central structure 330 shown in FIG. 25-A. Alternate sleeve 345a comprises grooves 345b equal to the amount of surrounding resilient members, such as extended resilient members 245 of embodiment 240 shown in FIG. 16, and are at least as wide as the resilient members. This feature enables the flexibility of the overall structure to be controlled by rotating cylinder 332 such that grooves 345b of alternate sleeves 345a either do or do not align with the surrounding resilient members. This effects the amount the extended resilient members can be compressed.

FIG. 25-D shows an alternate sleeve 347a that can be used to replace sleeves 331 in alternate central structure 330 shown in FIG. 25-A. Alternate sleeve 347a comprises grooves 347b, wherein the surfaces of the grooves are angled and are wider than the surrounding resilient members, such as extended resilient structure 245 of embodiment 240 shown in FIG. 16. This feature enables the flexibility of the overall structure to be controlled by rotating cylinder 332 such that the surrounding resilient members are at an arbitrary position and adjacent to the surfaces of grooves 347b of alternate sleeves 347a. Since the surfaces of grooves 347b are angled, the amount the surrounding resilient members can be compressed depends on the angular position of alternate sleeve 347a. Note that walls 348a, 348b exist to limit the rotational range of alternate sleeve 347a.

CONCLUSION, RAMIFICATIONS, AND SCOPE

Accordingly, the reader will see that the flexible structure of the present invention provides a simple structural configuration that possesses impact load dampening characteristics and high strength capabilities, while still exhibiting axial, bending, and/or twisting flexibility with respective restoring forces. The flexible structure has many applications, particularly in the fields of robotics and orthopedic braces. For example, the flexible structure can be used to construct robotic humanoid spines and orthopedic back braces, both of which require the ability to dampen high impact compressive loads, yet exhibit bending flexibility to allow motion of the robot or user.

While the above description contains many specificities, these should not be construed as limitations on the scope of the invention, but as exemplifications of the presently preferred embodiments thereof. Many other ramifications and variations are possible within the teachings of the invention. The resilient members located between each pair of adjacent formers can be of an arbitrary quantity and can be arranged in an arbitrary pattern, the resilient members can be affixed to the formers by using an arbitrary quantity of fasteners or weld joints, the resilient members and formers can have additional holes and cutouts to act as mounting provisions for equipment applicable to the application, the embodiment can comprise a variety of resilient members and formers each having a different size, etc.

Thus, the scope of the invention should be determined by the appended claims and their legal equivalents, and not by the examples given above.

I claim:

1. A flexible support structure comprising:
   (a.) two or more formers oriented in an offset configuration;
   (b.) a plurality of resilient members supporting and affixed to said formers, wherein each of said resilient members comprises at least one bend located between each of said formers;
   (c.) a central member located between each of said formers and central to said resilient members, wherein said central member has a surface with longitudinal grooves, wherein said central member can be rotated to a new angular position relative to said resilient members, thereby altering the thickness of said central member disposed between said resilient members, therefore altering the amount said resilient members can deform;
   wherein said flexible support structure can be incorporated into applications that require variable axial and bending compliance.

2. A flexible support structure comprising:
   (a.) two or more formers oriented in an offset configuration;
   (b.) a plurality of resilient members supporting and affixed to said formers, wherein each of said resilient members comprises at least one bend located between each of said formers;
   (c.) a central member located between each of said formers and central to said resilient members, wherein said central member is sized to stop excessive deformation of said resilient members;
   (d.) an element affixed to each former, wherein each said element comprises a protruding nose on one end and at least two walls extruding from the opposite end, wherein said nose and said walls are sized such that said walls of one said element surrounds said nose of an adjacent said element, thereby limiting relative twisting and tilting of said formers;
   wherein said flexible support structure can be incorporated into applications that require axial, bending, or twisting compliance, thereby mitigating the negative effects of impact loads.

3. A flexible support structure comprising:
   (a.) two or more formers oriented in an offset configuration;
   (b.) a plurality of resilient members supporting and affixed to said formers, wherein each of said resilient members comprises one bend located between each of said formers, wherein said resilient members are oriented so that the concavities of said bends of said resilient members open radially outward with respect to said flexible support structure;
   (c.) a surrounding member fitted between each of said formers and around said resilient members, wherein said surrounding member occupies the concavities of said bends of said resilient members and is sized to stop excessive deformation of said resilient members;
   (d.) an element affixed to each former, wherein each said element comprises a protruding nose on one end and at least two walls extruding from the opposite end, wherein said nose and said walls are sized such that said walls of one said element surrounds said nose of an adjacent said element, thereby limiting relative twisting and tilting of said formers;
   wherein said flexible support structure can be incorporated into applications that require axial, bending, or twisting compliance, thereby mitigating the negative effects of impact loads.

\* \* \* \* \*